(12) United States Patent
Jiang et al.

(10) Patent No.: US 11,091,791 B2
(45) Date of Patent: Aug. 17, 2021

(54) METHODS FOR HYBRIDIZATION BASED HOOK LIGATION

(71) Applicant: Complete Genomics, Inc., San Jose, CA (US)

(72) Inventors: Yuan Jiang, San Jose, CA (US); Radoje Drmanac, Los Altos Hills, CA (US)

(73) Assignee: MGI Tech Co., Ltd., Shenzhen (CN)

( * ) Notice: Subject to any disclaimer, the term of this patent is extended or adjusted under 35 U.S.C. 154(b) by 403 days.

(21) Appl. No.: 15/903,424

(22) Filed: Feb. 23, 2018

(65) Prior Publication Data

US 2018/0245132 A1    Aug. 30, 2018

Related U.S. Application Data

(60) Provisional application No. 62/463,182, filed on Feb. 24, 2017.

(51) Int. Cl.
*C12Q 1/68*       (2018.01)
*C12Q 1/6806*   (2018.01)

(52) U.S. Cl.
CPC .................................. *C12Q 1/6806* (2013.01)

(58) Field of Classification Search
None
See application file for complete search history.

(56) References Cited

U.S. PATENT DOCUMENTS

| | | |
|---|---|---|
| 7,303,901 B2 | 12/2007 | Hjorleifsdottir et al. |
| 9,217,167 B2 | 12/2015 | Heller et al. |
| 2004/0115616 A1 * | 6/2004 | Holton ............... C12N 15/64 435/5 |
| 2006/0110745 A1 * | 5/2006 | Hayashizaki ......... C12P 19/34 435/6.16 |
| 2007/0031942 A1 * | 2/2007 | Gao .................. C12Q 2565/543 435/91.2 |
| 2008/0003571 A1 | 1/2008 | McKernan et al. |

(Continued)

FOREIGN PATENT DOCUMENTS

| WO | WO-2010051773 A1 * | 5/2010 | ........... C12Q 1/6869 |
|---|---|---|---|
| WO | 2010/094040 A1 | 8/2010 | |

OTHER PUBLICATIONS

Clusel et al. (Nucleic Acids Research, 1993 21(15), p. 3407-3411) (Year: 1993).*

(Continued)

*Primary Examiner* — Stephanie K Mummert
(74) *Attorney, Agent, or Firm* — Kilpatrick Townsend & Stockton LLP

(57) ABSTRACT

Provided herein are compositions, methods, and kits for enriching for one or more nucleic acid sequences of interest in a sample. The methods include providing a circular ligase, one or more 5' hook probes and/or one or more 3' hook probes and contacting the sample comprising the nucleic acids with the circular ligase and one or more 5' hook probes and/or one or more 3' hook probes under conditions to allow the hook probes to selectively bind to the one or more nucleic acid sequences of interest, and under conditions to form one or more hook products, each hook product comprising the hook probes and the one or more nucleic acid sequences of interest.

19 Claims, 10 Drawing Sheets

Specification includes a Sequence Listing.

(56) References Cited

U.S. PATENT DOCUMENTS

2009/0061424 A1* 3/2009 Chen .................. C12Q 1/6809
435/6.12
2012/0004126 A1 1/2012 Drmanac et al.

OTHER PUBLICATIONS

Blondal et al. (Nucleic Acids Research, 2005, 33(1):135-142, IDS reference) (Year: 2005).*
Adessi, C. et al. "Solid phase DNA amplification: characterisation of primer attachment and amplification mechanisms." Nucleic Acids Research, vol. 28, Issue 20. Published Oct. 15, 2000. pp. e87.
Brenner, S. et al. "Gene expression analysis by massively parallel signature sequencing (MPSS) on microbead arrays" Nature Biotechnology, vol. 18. Published Jun. 1, 2000. pp. 630-634.
Blondal et al. "Isolation and characterization of a thermostable RNA ligate 1 from a *Thermus scotoductus* bacteriophage TS2126 with good single-stranded DNA ligation properties." Nucleic Acids Research. vol. 33, No. 1. Published Jan. 2005. pp. 135-142.
Drmanac, R. et al. "Accurate Whole Genome Sequencing as the Ultimate Genetic Test," Clinical Chemistry 61.1 (2015): 305-306.
Drmanac, R. et al. "Human genome sequencing using unchained base reads on self-assembling DNA nanoarrays," Science 327.5961 (2010): 78-81.
Drmanac, S. et al. "Accurate sequencing by hybridization for DNA diagnostics and individual genomics," Nat. Biotechnol. 16, 54-58 (1998).
Li et al. "Structure-independent and quantitative ligation of single-stranded DNA." Analytical Biochemistry, vol. 349, Issue 2. Published Feb. 15, 2006. pp. 242-246.
Lucks et al. "Multiplexed RNA structure characterization with selective 2'-hydroxyl acylation analyzed by primer extension sequencing (SHAPE-Seq)." Proc. Natl. Acad. Sci. USA, vol. 108, Issue 27. Published Jul. 2011. pp. 11063-11068.
Mamanova et al. "Target-enrichment strategies for next-generation sequencing." Nature Methods, 7. Published Jan. 2010. pp. 111-118.
Margulies, M. et al. "Genome sequencing in microfabricated high-density picolitre reactors," Nature 437.7057 (2005): 376-380.
Meng, H-M et al. "DNA dendrimer: an efficient nanocarrier of functional nucleic acids for intracellular molecular sensing," ACS Nano 8.6 (2014): 6171-6181.
Metzker, Michael L. "Sequencing technologies—the next generation," Nature Reviews Genetics 11.1 (2010): 31-46.
Ng, S. et al. "Targeted capture and massively parallel sequencing of 12 human exomes," Nature 461.7261 (2009): 272-276.
Ronaghi et al. "Real-time DNA sequencing using detection of pyrophosphate release" Anal. Biochem. 242, 84-89 (1996).
Shendure, J. et al. "Accurate multiplex polony sequencing of an evolved bacterial genome," Science 309, 1728-1732 (2005).
Shendure, J., et al. "Advanced sequencing technologies: methods and goals" Nat. Rev. Genet. 5, 335-344 (2004).
Shendure, J., et al "Next-generation DNA sequencing," Nature biotechnology 26.10 (2008): 1135-1145.
Tessier et al. "Ligation of Single-Stranded Oligodeoxyribonucleotides by T4 RNA Ligase." *Analytical Biochemistry*, vol. 158, issue 1. Published Oct. 1986. pp. 171-178.
Zhang et al. "Single-stranded DNA ligation by T4 RNA ligase for PCR cloning of 54-noncoding fragments and coding sequence of a specific gene." Nucleic Acids Research, vol. 24, No. 5. 1996. pp. 990-991.

* cited by examiner

METHODS FOR HYBRIDIZATION BASED HOOK LIGATION

CROSS-REFERENCES TO RELATED APPLICATIONS

This application claims priority to U.S. Provisional Patent Application No. 62/463,182, filed Feb. 24, 2017, the content of which is incorporated by reference in its entirety.

REFERENCE TO A "SEQUENCE LISTING" SUBMITTED AS ASCII TEXT FILES VIA EFS-WEB

The Sequence Listing written in file 092171-1077175-5054-US_SequenceListing.txt created on May 18, 2018, 1,450 bytes, machine format IBM-PC, MS-Windows operating system, in accordance with 37 C.F.R. §§ 1.821- to 1.825, is hereby incorporated by reference in its entirety for all purposes.

BACKGROUND

Sample preparation for high-throughput nucleic acid sequencing or other techniques may involve an enrichment step that increases the ratio of target nucleic acids to non-target nucleic acids in a sample. Such enrichment steps can take advantage of a number of different physico-chemical attributes of the target and non-target nucleic acids. See, Mamanova et al., Nat. Methods, 7:111-118 (2010). For example, target nucleic acids having known sequence attributes can be enriched by selecting nucleic acid fragments having the target nucleic acid sequences of interest from a sample. In particular, elevated temperature (e.g., 65° C.) hybridization of target nucleic acids to labeled oligonucleotides (known as bait oligonucleotides) can be used for enrichment of a set of nucleic acids having the target sequences (i.e., target nucleic acids), a process generally referred to as "hybrid capture." In one approach hybrid-capture enrichment methods can use RNA bait oligonucleotides, which form RNA:DNA hybrids with target nucleic acids.

Hybrid capture methods are well-suited to high throughput sequencing work flows that require highly parallelized sample preparation. For high throughput sequencing sample preparation, the specificity of the hybridization reaction between bait oligonucleotides and sample nucleic acids can be enhanced by including blocking nucleic acid such as CoT-1 DNA and/or sequence specific blocking oligonucleotides.

However, typical hybrid capture methods known in the art can require very long hybridization times to reach equilibrium and/or achieve efficient capture and enrichment of target nucleic acids. Moreover, although hybrid capture methods known in the art do enrich samples for target nucleic acids, there is still a significant level of undesirable non-target nucleic acid contamination. Non-target contamination can reduce the probability of detecting rare mutations in enriched nucleic acid samples by high throughput sequencing. Furthermore, a significant fraction of target nucleic acids can be lost during hybridization, washing, harvesting, or during processing steps upstream (e.g., adaptor ligation) or downstream (e.g., flow cell immobilization) of the hybridization step. Thus, there remains a need in the art for methods, compositions, instrumentation, and systems for improved enrichment methods. Certain embodiments of the present invention address one or more of these needs.

BRIEF SUMMARY

Provided herein are compositions, methods, and kits for producing hook probe products and for enriching for one or more nucleic acid sequences from a sample comprising a heterogeneous mixture of nucleic acid fragments comprising different nucleic acid sequences. The methods include providing a ligase, one or more 5' hook probes and/or one or more 3' hook probes, combining the sample, ligase and hook probes under conditions to allow the hook probes to selectively bind to the one or more nucleic acid fragments of interest, and under conditions to form one or more hook products, each hook product comprising the hook probes and the one or more nucleic acid sequences of interest.

DETAILED DESCRIPTION

Figure 1:
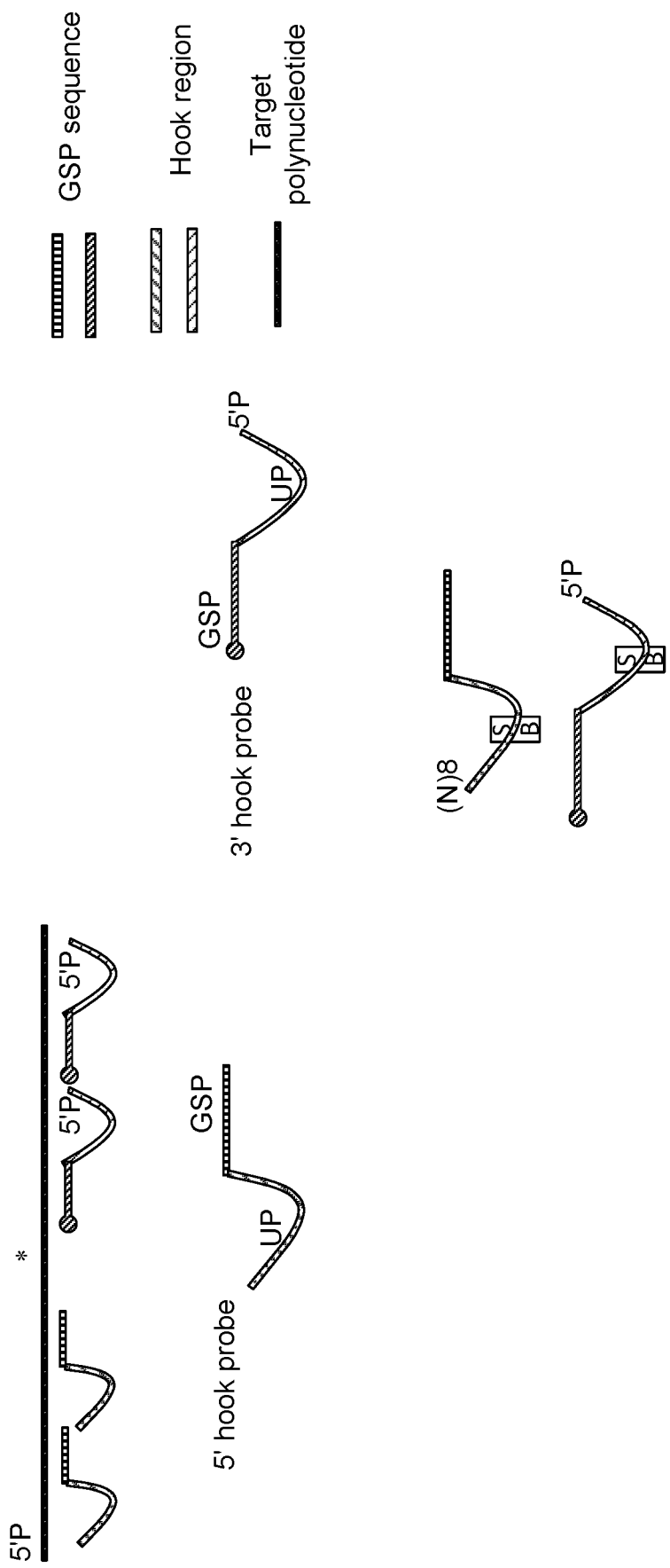
FIG. 1 is a schematic showing 5' and 3' hook probes with target sequence regions complementary to nucleic acid sequences of interest in a target polynucleotide. The target polynucleotide, comprising a sequence of interest, is identified by an asterisk. The hook probe(s) can hybridize near a terminus of the target nucleic acid.

It is frequently useful to enrich for particular polynucleotide sequences. For example, in a sample comprising polynucleotides representing an entire genome, it may be useful to enrich for polynucleotides comprising exome sequences or transcriptome sequences. The enriched polynucleotides can be interrogated (e.g., sequenced) more efficiently, more accurately, and/or at lower cost than the unenriched sample. As another example, in a sample comprising cDNA or genomic DNA it may be useful to enrich for polynucleotides comprising specified markers, polymorphic regions, SNPs, insertions, deletions, duplications, or other variations, for interrogation. For example, a patient sample may be enriched for genomic DNA or cDNA fragments that contain a predetermined panel of tumor marker sequences for diagnosis or prognosis.

Hook products comprising exome sequences, transcriptome sequences, specified markers, polymorphic regions, SNPs, insertions, deletions, duplications, or other variations, may be produced and interrogated to provide diagnostic, prognostic, or other information. Provided herein are methods for producing hook probe products and for enriching for one or more nucleic acid sequences of interest in a sample using hook probes to produce hook products.

In one approach the method for producing a hook probe product comprises combining (i) a heterogeneous mixture of nucleic acid fragments, wherein at least a first fragment in the mixture comprises the nucleic acid sequence of interest, (ii) one or more 5' hook probes comprising a hook region and a target region complementary to a sequence in the first fragment, (iii) one or more 3' hook probes comprising a hook region and a target region complementary to a sequence in the first fragment, and (iv) a ligase (such as a ssDNA or RNA ligase), wherein (i)-(iii) are combined under conditions in which at least one 5' hook probe and at least one 3' hook probe selectively bind the first fragment, and wherein (i)-(iv) are combined under conditions in which a 5' hook probe terminus is ligated to the 5' terminus of the first fragment and a 3' hook probe terminus is ligated to the 3' terminus of the first fragment, thereby producing a hook probe product, wherein the hook probe product comprises the nucleic acid sequence of interest. Multiple steps of combining and addition of ligase can be performed. Optionally, the ligase is a circular ligase.

In one approach, the method includes providing a ligase (such as a ssDNA or RNA ligase), one or more 5' hook probes comprising a target specific region and a hook region, and/or one or more 3' hook probes comprising a target specific region and a hook region and contacting the sample comprising the nucleic acids with the one or more 5' hook probes, the one or more 3' hook probes, and the ligase under conditions to allow the hook probes to selectively bind to the one or more nucleic acid sequences of interest and under conditions resulting in formation of one or more hook products. Optionally, the ligase is a circular ligase.

Each hook product comprises a 5' hook probe ligated to the 5' terminus of a nucleic acid fragment comprising a nucleic acid sequence of interest and/or a 3' hook probe ligated to the 3' terminus of the nucleic acid fragment comprising the sequence of interest. The formation of hook products can include multiple steps of ligation. For example, a 5' hook probe may be ligated to the terminus of a nucleic acid fragment comprising a nucleic acid sequence of interest in one step and in a subsequence step, a 3' hook probe may be ligated to the terminus of a nucleic acid fragment comprising a nucleic acid sequence of interest.

As used herein, the terms "nucleic acid sequence of interest" or "target sequence of interest" refer to a polynucleotide sequence to be analyzed, interrogated (e.g., sequenced) or quantitated. Typically, many different nucleic acid sequences of interest are simultaneously analyzed, interrogated or quantitated from a single sample. Nucleic acid sequences of interest include, but are not limited to, coding regions, intron regions, genes, exons, cDNA, promoters, enhancers, or fragments thereof of interest. Nucleic acid sequences of interest can be sequences that include, for example, a single nucleotide polymorphism (SNP), an indel (insertion or deletion), a fusion, a copy number variation or any combination thereof.

As used herein, the terms "target nucleic acids" and "target polynucleotides" are used herein to refer to a polynucleotide (e.g., a genomic fragment) containing a nucleic acid sequence (or "target sequence") of interest or target sequence of interest. As used herein, "non-target nucleic acids" are polynucleotides in a sample or mixture that do not comprise a nucleic acid sequence of interest. The methods may be used to enrich target nucleic acids from a sample containing both target nucleic acids and non-target nucleic acids.

As used herein, the term "nucleic acid fragments," refers to polynucleotides in a heterogeneous mixture of polynucleotides. For example, genomic DNA can be fragmented to produce a mixture of nucleic acid fragments. The term "fragments" is used for convenience without specifying a specific method of production. For example, fragmented genomic DNA, cDNA produced from mRNA, and cell free (cf) DNA all can be referred to as nucleic acid fragments. According to the present invention, a sample may contain a heterogeneous mixture of nucleic acids some of which are "target nucleic acids" comprising nucleic acid sequences of interest.

Hook Probes

A hook probe may be a 5' hook probe or a 3' hook probe. The herein provided hook probes include a target specific region (TSR) and a hook region (HR). The target specific region is designed to hybridize to a complementary sequence in a target nucleic acid in a sample. The hook region of the 5' hook probe can include a universal primer binding site, a unique molecular identifier, a sample barcode, a cell barcode, other useful elements, or any combination thereof. Similarly, the hook region of the 3' hook probes can include a universal primer binding site, a unique molecular identifier, a sample barcode, a cell barcode, other useful elements, or any combination thereof. Generally, it is advantageous that the hook region does not hybridize to the target nucleic acids in the sample and may be designed to this end.

Target Specific Region (TSR)

The target specific region in the hook probes can have any suitable length and sequence for target-specific hybridization to a target nucleic acid or nucleic acid fragment in a reaction mixture containing both target and non-target nucleic acids. The length of the target specific region is generally less than 200 nucleotides. By way of example, the length of the target specific region can be from 10 to 100 nucleotides, in the range of 18 to 200 nucleotides, from 20 to 200 nucleotides, from 25 to 200 nucleotides, from 30 to 200 nucleotides, from 50 to 200 nucleotides, from 18 to 100 nucleotides, from 20 to 100 nucleotides, from 25 to 100 nucleotides, from 30 to 100 nucleotides, from 35 to 100 nucleotides, from 40 to 100 nucleotides, from 50 to 100 nucleotides, from 60 to 100 nucleotides, from 10 to 75 nucleotides, from 18 to 75 nucleotides, from 20 to 75 nucleotides, from 25 to 75 nucleotides, from 30 to 75 nucleotides, from 35 to 75 nucleotides, from 40 to 75 nucleotides, from 50 to 75 nucleotides, from 60 to 75 nucleotides, from 18 to 50 nucleotides, from 20 to 50 nucleotides, from 25 to 50 nucleotides, from 30 to 50 nucleotides, from 35 to 50 nucleotides, from 40 to 50 nucleotides, from 18 to 40 nucleotides, from 20 to 40 nucleotides, from 25 to 40 nucleotides, from 30 to 40 nucleotides, from 35 to 40 nucleotides, from 18 to 35 nucleotides, from 20 to 35 nucleotides, or from 25 to 35 nucleotides, from 30 to 35 nucleotides, from 18 to 30 nucleotides, from 20 to 30 nucleotides, or from 25 to 30 nucleotides.

Figure 2:
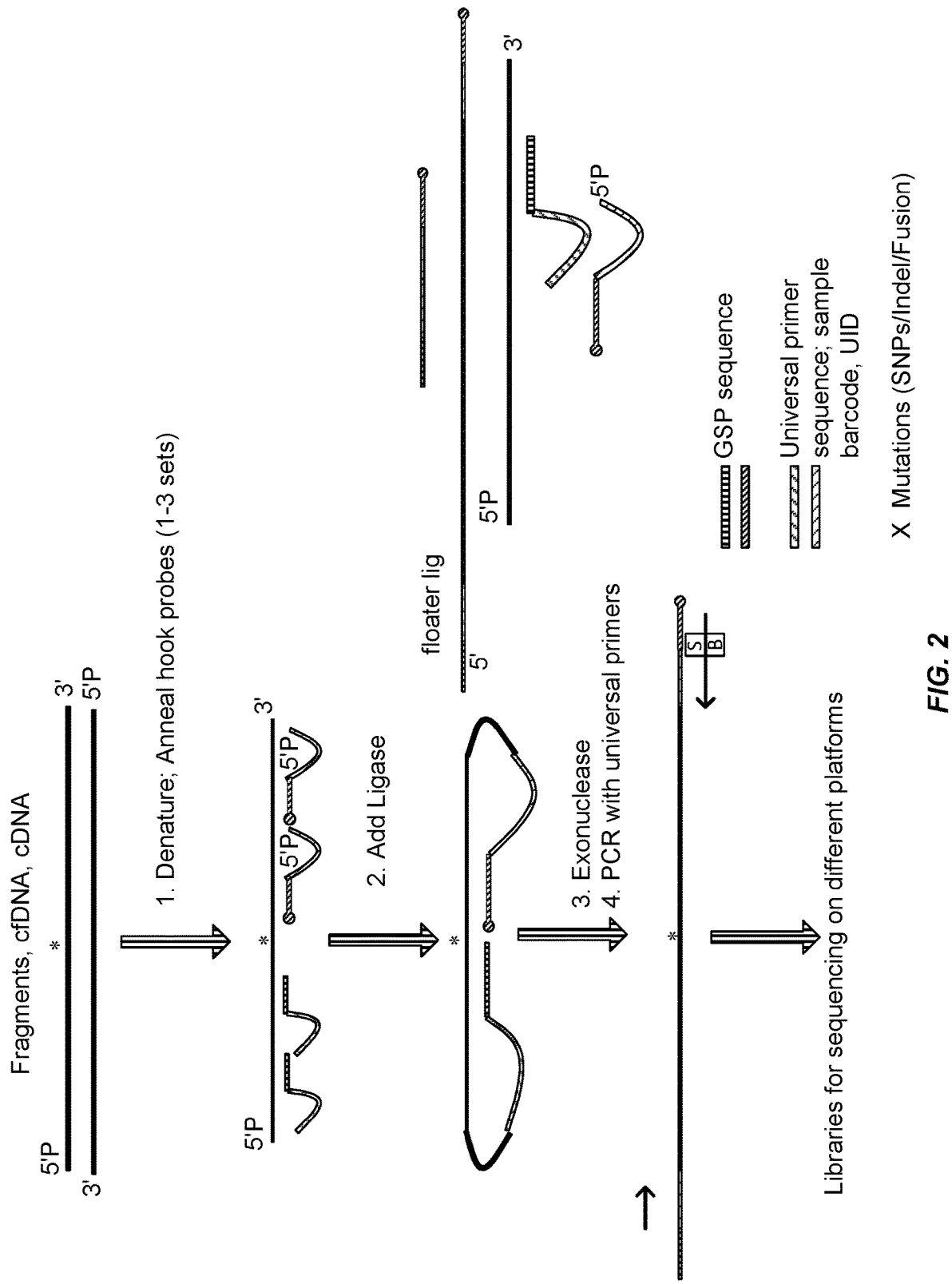
FIG. 2 is a schematic of an exemplary method using hook probes. DNA (e.g., fragmented genomic DNA or cell-free DNA) can be denatured (e.g., by heat) followed by contacting with one or more hook probes or hook probe sets. The hook probes bind the nucleic acid sequences of interest (represented by the asterisk) and one 5' hook probe and one 3' hook probe are ligated to the 5' and 3' termini, respectively, of the target nucleic acid to form hook products. Floater ligation products that do not contain target DNA, along with other single stranded nucleic acids, can be degraded using exonucleases. Hook products can be amplified using universal primers that optionally contain sample barcode(s) (SB).

As illustrated in FIG. 2, hook probes may be designed so that more than one hook probes can be used to produce hook products with a given sequence of interest. A combination of hook probes designed to capture the same sequence of interest can be called a hook probe set. A hook probe set can comprise one 5' hook probe and one 3' hook probe. In other embodiments, hook probe set can comprise more than one 5' hook probe and/or more than one 3' hook probe. In other embodiments, hook probe set can comprise more than two 5' hook probes and two 3' hook probes, as illustrated in FIG. 2.

In some embodiments, the hook probes are designed to flank the sequence(s) of interest. For illustration, a pair of hook probes may be complementary to sequences in the nucleic acid fragment that flank a sequence of interest in the fragment. For illustration, a pair of hook probes may flank a sequence comprising a single nucleotide polymorphism. In another illustration, the probe binding sites may flank a sequence linked (i.e., in LD) to a SNP or other polymorphism. In some embodiments, a sequence of interest may be contained within, or partly contained within a hook probe binding site(s).

Hook Region (HR)

The hook regions of the hook probes are designed so they do not hybridize to the target nucleic acid under hybridization, template-dependent primer extension, or primer mediated amplification conditions, or a combination thereof. In some cases, the sequence of the hook region can be selected such that it is not complementary (e.g., exactly complementary or sufficiently complementary to hybridize) to any expected sequence in a sample containing target polynucleotides. For example, where a sample is a sample of human genomic DNA, the sequence of the hook region can be selected such that it not complementary to any region in the human genome. As another example, where a sample is a sample of human genomic DNA, the sequence of the hook region can be selected such that no portion of the hook region is exactly complementary to more than 6, 7, 8, 9, 10, 11, 12, 13, 14, 15, 16, 17, or 18 contiguous nucleotides of the human genome. As yet another example, where a sample is a sample of human genomic DNA, the sequence of the hook region can be selected such that it differs in at least 1, 2, 3, 4, 5, 6, 7, 8, 9, 10, 11, 12, 13, 14, 15, 16, 17, or 18 positions from any contiguous sequence of human genomic DNA (e.g., any contiguous sequence having the same length as the hook region).

The length of the hook region can be any suitable length. Typically, the hook region is selected such that the total length of the hook region is, is less than, or is less than about, 200, 175, 125, 100, 75, 70, 60, 55, 50, 45, 40, 35, 30, or 25 nucleotides. For example, the hook region can have a length of from about 4 to 50 nucleotides, from 4 to 40 nucleotides, from 4 to 35 nucleotides, from 4 to 30 nucleotides, from 4 to 25 nucleotides, from 4 to 20 nucleotides, from 4 to 18 nucleotides, from 4 to 15 nucleotides, from 4 to 12 nucleotides, from 4 to 10 nucleotides from 4 to 8 nucleotides, or from 4 to 6 nucleotides. In some cases, the hook region has a length of 7 to 30, 7 to 25 nucleotides, 7 to 20 nucleotides, 7 to 18 nucleotides, 7 to 15 nucleotides, 7 to 12 nucleotides, or 7 to 10 nucleotides. In some cases, the hook region is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In various embodiments the hook region may comprise one or more elements selected from a primer binding site or universal primer binding site, a unique molecular identifier (UMI), a barcode, such as a cellular barcode, a sample barcode, or other barcode, other useful elements, or any combination thereof.

Universal Primer Binding Site

The hook region can contain a universal primer binding site or the complement of a universal primer binding site. As used herein, "universal primer binding site" has it usual meaning in the art, and refers to a nucleic acid region having a sequence shared amongst all, or a substantial fraction of all, 5' and/or 3' hook probes in a reaction mixture which can be hybridized to a universal primer under primer hybridization conditions (e.g., PCR primer annealing conditions or ligation conditions). Optionally, the polynucleotides are the portion of polynucleotides ligated to the hook probes containing the universal primer binding site. In some embodiments, the 3' hook probes contain a different universal priming site from the 5' hook probes. Thus, the 5' hook probe and 3' hook probe can together comprise a forward universal primer binding site or its complement and a reverse universal primer binding site or its complement. A single forward universal primer and a single reverse universal primer can be used to amplify any region of interest that is positioned between the forward and reverse universal primer binding sites of different target polynucleotides, independent of the sequence of the region of interest. Moreover, multiple different sets of universal primers can be utilized to amplify hook products containing multiple different sets of universal primer binding sites. Where two different forward and two different reverse universal primers are used, about 25% of the hook regions in a reaction mixture can share the same universal primer binding site sequence.

Such universal primer binding sites (or their complement) can be useful for providing a hook product that can be further amplified by universal PCR. Thus, the hook probes can be used for target-specific selection and/or amplification, e.g., from a complex mixture, and the selected target(s) can be universally amplified in a subsequent or simultaneous step. The universal primer binding site (or its complement) can be the entire hook region or a portion thereof. The universal primer binding site (or its complement) can include the 3'-most nucleotide of the hook region, the 5'-most nucleotide of the hook region, or the 3'-most and 5'-most nucleotide of the hook region. Typically, the universal primer binding site (or its complement) is selected to have a length sufficient to allow target-specific hybridization of a universal primer. Thus, the universal primer binding site can have a length of from 10 to 25 nucleotides, from 10 to 20 nucleotides, from 10 to 18 nucleotides, from 10 to 15 nucleotides, or from 10 to 12 nucleotides. In some cases, the universal primer binding site has a length of 7 to 30, 7 to 25 nucleotides, 7 to 20 nucleotides, 7 to 18 nucleotides, 7 to 15 nucleotides, 7 to 12 nucleotides, or 7 to 10 nucleotides. In some cases, the universal primer binding site is 4, 5, 6, 7, 8, 9, 10, 11, 12, 13, 14, 15, 16, 17, 18, 19, 20, 21, 22, 23, 24, or 25, nucleotides in length. Typically, the universal primer binding site (or its complement) is selected to have a sequence that is different from the sequence of one or more, or all, target polynucleotide sequences of the same length at 1, 2, 3, 4, 5, 6, 7, 8, 9, 10 or more positions.

Unique Molecular Identifier (UMI)

Each 5' and/or 3' hook probe can include one or more unique molecular identifier (UMI). The unique molecular identifier can be located in the hook region of the hook probe. In some embodiments, the hook region can contain a molecular identifier that is different for every hook probe. In some embodiments, the unique molecular identifier is about 3-12 nucleotides in length, or 3-5 nucleotides in length. In some cases, each unique molecular identifier is about 3-12 nucleotides in length, or 3-5 nucleotides in length. Thus, a unique molecular identifier can be 3, 4, 5, 6, 7, 8, 9, 10, 11, 12, 13, 14, 15 or more nucleotides in length.

Barcode

In some embodiments, the hook region can include a barcode that identifies a set of target sequences with a common feature. For example, the chromosomal barcodes may identify the chromosomal location of the target sequence (e.g., Y-chromosome target sequences can have a common barcode, and X-chromosome target sequences can have a different common barcode). As another example, the hook region can contain a cellular barcode that is the same for every hook probe in a single-cell reaction (e.g., a reaction in which the target nucleic acids in the sample are all from a single cell) but different for hook probes in different reactions directed to target nucleic acids from a different cell. Optionally, the hook region can include a sample barcode. As another example, the hook region can contain a cell barcode, a chromosomal barcode, and a sample barcode or any combination thereof. In some embodiments, the barcode region is about 3-12 nucleotides in length, or 3-5 nucleotides in length. In some cases, each barcode of the barcode region is about 3-12 nucleotides in length, or 3-5 nucleotides in length. Thus, a barcode, whether sample barcode, cell barcode or other barcode can be 3, 4, 5, 6, 7, 8, 9, 10, 11, 12, 13, 14, 15 or more nucleotides in length.

Cleavage Sites and Modified Nucleotides of Hook Probes

Optionally, the hook probes comprise a restriction enzyme binding site that can be cleaved with a restriction enzyme. Thus, the provided methods can include contacting the hook products with a restriction enzyme. Optionally, the restriction enzyme cleaves the target specific probe from the hook products. See for example, FIG. 3.

In some embodiments, the hook probes comprises one or more modified nucleotides capable of being cleaved. Cleavage of the hook probe at the modified nucleotide also removes the target specific probe from the hook products producing a product suitable for amplification by universal primers or a product suitable for circularization and amplification by rolling circle amplification. Suitable examples of modified nucleotide/enzyme combinations include, but are not limited to, (i) deoxyuridine and E. coli Uracil DNA glycosylase (UDG) or A. fulgidis UDG (Mu UDG) in combination with one or more enzymes that can remove an AP site, such as, human apurinic/apyrimidinic (AP) endonuclease (APE 1), Endonuclease III (Endo III), Endonuclease IV (Endo IV), Endonuclease VIII (Endo VIII), formamidopyrimidine [fapy]-DNA glycosylase (Fpg), human 8-oxoguanine glycosylsase (hOGG1), or human Nei-like Glycosylase 1 (hNEIL1)Endonuclease VIII (Endo VIII); (ii) deoxyinosine and Endonuclease V, or Human 3-alkyladenine DNA glycosylase (hAGG) to generate an AP site and one or more enzymes that can remove an AP site, such as, APE 1, Endo III, Endo IV, Endo VIII, Fpg, hOGG1, or hNEIL1; (iii) oxidized pyrimidine nucleotide (e.g., 5, 6-dihydroxythymine, thymine glycol, 5-hydroxy-5-methylhydantoin, uracil glycol, 6-hydroxy-5, 6-dihydrothymine, or methyltartronylurea) and Endo VIII, Endo III, hNEIL1, or a combination thereof; (iv) oxidized purine nucleotide (e.g., 8-oxoguanine, 8-hydroxyguanine, 8-oxoadenine, fapy-guanine, methy-fapy-guanine, or fapy-adenine) and Fpg, hOGG1, hNEIL1, or a combination thereof; (v) alkylated purine (e.g., 3-mehtyladenine, 7-methylguanine, 1,N6-ethenoadenine, and hypoxanthine) and hAGG to generate an AP site and one or more enzymes that can remove an AP site, such as, APE 1, Endo III, Endo IV, Endo VIII, Fpg, hOGG1, or hNEIL1; and (vi) 5-hydroxyuracil, 5-hydroxymethyluracil, or 5-formyluracil and human single-strand-selective monofunctional uracil-DNA Glycosylase SMUG1 (hSMUG1) to generate an AP site and one or more enzymes that can remove an AP site, such as, APE 1, Endo III, Endo IV, Endo VIII, Fpg, hOGG1, or hNEIL1.

Ligatable Termini of Hook Probes

Hook probes comprise a ligatable terminus capable of being ligated to a single-stranded end of a target nucleic acid.

5' hook probes have a functional 3' OH group capable of being ligated to the 5' end of a target nucleic acid. Optionally, the 5' end of the 5' hook probes contains a blocking group.

3' hook probes include a functional 5' phosphate capable of being ligated to the 3' end of a target nucleic acid. Optionally, the 3' end of the 3' hook probes contain a 3' blocking group.

Blocking groups are known and include, for example, a 3' phosphate, a 3' ring-opened sugar such as a 3'-phospho-α, β-unsaturated aldehyde (PA), 3' amino modifier, 3' dideoxynucleotide, 3' phosphorothioate (PS) bond, or a 3' phosphate ester. As used herein, "blocked" ends (i.e., nucleic acid termini with a blocking group) cannot be ligated to another nucleic acid even when hybridized to a target nucleic acid.

In some embodiments, the 5' hook probes have the structure: 5'-(target specific region)-(hook region)-3'. Optionally, the 5' hook probes have the structure 5'-(target specific region)-(unique molecular identifier)-(universal primer binding site)-3'. In some embodiments, the 3' hook probes have the structure 5'-(hook region)-(target specific region)-3'. Optionally, the 3' hook probes have the structure: 5'-(universal primer binding site)-(unique molecular identifier)-(target specific region)-3'.

Sources of Target Nucleic Acids and Samples Comprising Target Nucleic Acids

In some aspects, provided is a method for producing a hook probe product comprising a nucleic acid sequence of interest from a heterogeneous mixture of nucleic acid fragments that includes target nucleic acids. The mixture can be referred to as a sample. Target nucleic acids in the sample can be double or single-stranded, or may contain portions of both double-stranded and single-stranded regions. For example, target nucleic acids in the sample can be single- or double-stranded genomic DNA, single- or double-stranded cDNA, mRNA, or a DNA/RNA hybrid (e.g., mRNA hybridized to first strand cDNA). In some embodiments, the target polynucleotides are genomic DNA. In some embodiments, the target polynucleotides are cDNA. In some embodiments, the target polynucleotides are synthetic DNA.

In some embodiments, target nucleic acids comprise genomic DNA. In some embodiments, target nucleic acids comprise a subset of a genome (e.g., a subset of interest for a particular application, e.g., selected regions of the genome that may harbor mutations in a particular subset of a population such as individuals predisposed to cancer). In some embodiments, target nucleic acids comprise exome DNA. In some embodiments, target nucleic acids comprise all or part of a transcriptome. In some embodiments, target nucleic acids comprise all or part of a microbiome or microbiota. In some embodiments, target nucleic acids comprise all or part of a methylome, i.e., the population of methylated sites and the pattern of methylation in a genome or in a particular cell. Optionally, the sample comprises cell free DNA. Optionally, the sample comprises RNA. Optionally, the sample comprises genomic DNA from cells, tissues, FFPE samples, or whole blood.

Sources

Samples containing target nucleic acids can be obtained from any suitable source. For example, the sample can be obtained or provided from any organism of interest. Such organisms include, for example, plants; animals (e.g., mammals, including humans and non-human primates); or pathogens, such as bacteria and viruses. In some cases, the sample can be, or can be obtained from, cells, tissue, or polynucleotides of a population of such organisms of interest. As another example, the sample can be a microbiome or microbiota. Optionally, the sample is an environmental sample, such as a sample of water, air, or soil.

Samples from an organism of interest, or a population of such organisms of interest, can include, but are not limited to, samples of bodily fluids (including, but not limited to, blood, urine, serum, lymph, saliva, anal and vaginal secretions, perspiration and semen); cells; tissue; biopsies, research samples (e.g., products of nucleic acid amplification reactions, such as PCR amplification reactions); purified samples, such as purified genomic DNA; RNA preparations; and raw samples (bacteria, virus, genomic DNA, etc.). Methods of obtaining target polynucleotides (e.g., genomic DNA) from organisms are well known in the art.

Fragmentation of Target Nucleic Acids

In some embodiments, target nucleic acids (e.g., genomic DNA) are processed by fragmentation to produce fragments of one or more specific sizes or to produce a population of fragments having a narrow distribution of fragment lengths. Any method of fragmentation can be used. For example, in some embodiments, the target nucleic acids are fragmented by mechanical means (e.g., ultrasonic cleavage, acoustic shearing, needle shearing, nebulization, or sonication); by chemical methods (e.g., heat and divalent metal cation); or by enzymatic methods (e.g., using endonucleases, nickases, or transposases). Methods of fragmentation are known in the art; see e.g., US 2012/0004126. In some embodiments, fragmentation is accomplished by ultrasound (e.g., Covaris or Sonicman 96-well format instruments).

Although some target nucleic acids (e.g., genomic DNA) can fragment during routine manipulation, the methods, compositions, and kits described herein can be used with very large target nucleic acids, at least in part because multiple different probes can target different regions of a single target nucleic acid. Thus, in some embodiments, target nucleic acids need not be subject to an active fragmentation step. For example, in some cases, target nucleic acids are not fragmented, not nebulized, not sheared (e.g., hydrodynamically sheared, chemically sheared, or acoustically sheared), not sonicated, not fragmented with a non-specific nuclease (e.g., DNase I) or a restriction nuclease (e.g., a 4-cutter), or not fragmented with a transposase (e.g., tagmentase).

It will be appreciated that the process of fragmentation of target nucleic acids in a sample generally also results in the fragmentation of non-target nucleic acids in the sample.

Ligatable Termini of Target Polynucleotides

Target nucleic acids are prepared (e.g., fragmented, reverse transcribed) so that one or both termini of the nucleic acid is ligatable to a hook probe terminus in the presence of ligase.

Size-Selection of Nucleic Acid Fragments

In some embodiments, target nucleic acids or nucleic acid fragments (e.g., fragmented genomic DNA or RNA) are subjected to a size selection step to obtain nucleic acid fragments having a certain size or distribution of sizes. Any methods of size selection can be used. For example, in some embodiments, fragmented target nucleic acids are separated by gel electrophoresis and the band or region corresponding to a fragment size or range of sizes of interest is extracted from the gel. In some embodiments, a spin column can be used to select for fragments having a certain minimum size. In some embodiments, paramagnetic beads can be used to selectively bind DNA fragments having a desired range of sizes. In some embodiments, solid-phase reversible immobilization (SPRI) methods can be used to enrich a sample for fragments having a certain size or distribution of sizes. In some embodiments, a combination of size selection methods can be used.

In some embodiments, target nucleic acids or fragmented target nucleic acids are about 50 to about 3000 bases in length, e.g., from about 50 to about 600 bases in length, from about 300 to about 1000 bases in length, from about 300 to about 600 bases in length, or from about 200 to about 3000 bases in length. In some embodiments, the target nucleic acids or fragmented target nucleic acids are 25-100, 50-100, 50-200, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, or 2000-3000 bases in length. In some embodiments, at least 25%, 50%, 75%, or 90% of target nucleic acids or fragmented target nucleic acids in a sample (e.g., a purified sample) are about 50 to about 2000 bases in length, e.g., from about 50 to about 600 bases in length, from about 300 to about 1000 bases in length, from about 300 to about 600 bases in length, or from about 200 to about 2000 bases in length. In some embodiments, at least 25%, 50%, 75%, or 90% of target nucleic acids or fragmented target nucleic acids in a sample are 25-100, 50-100, 50-200, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, or 1750-3000 bases in length. In some embodiments, the target nucleic acids or fragmented target nucleic acids (e.g., genomic DNA) have a mean length of about 50, about 100, about 150, about 200, about 250, about 300, about 350, about 400, about 450, about 500, about 550, about 600, about 650, about 700, about 750, about 800, about 850, about 900, about 950, about 1000, about 1100, about 1200, about 1300, about 1400, about 1500, about 1600, about 1700, about 1800, about 1900, about 2000, or about 3000 bases in length.

Ligases

Hook probes are used in combination with one or more ligases. Ligases of interest are capable (under appropriate conditions and with appropriate substrates) of intermolecular ligation of polynucleotides with single-stranded termini. Optionally, the ligase is a ssDNA or RNA ligase. In one aspect the ligase is referred to as a "circular ligase." As used herein, the term "circular ligase" refers to an enzyme that catalyzes the formation of a covalent phosphodiester bond between two distinct or separate nucleic acid strands. For example, the ligases catalyze the synthesis of a phosphodiester bond between the 3'-hydroxyl group of one polynucleotide, and the 5'-phosphoryl group, of a second polynucleotide. In some cases, hybridization of the hook probes to a target nucleic acid can produce a substrate for ligation. For example, hybridization of a 5' hook probe to a target nucleic acid can produce a 3' hydroxyl group suitable for ligation to the 5' terminus of the target nucleic acid. Optionally, the 5' hook probe comprises a blocked 5' end that is not suitable for ligation. Similarly, hybridization of a 3' hook probe to a target nucleic acid can produce a free 5' phosphate that can be ligated to the 3' terminus of the target nucleic acid. Optionally, the 3' hook probes comprises a blocked 3' end that is not suitable for ligation.

In some embodiments, the circular ligase is an RNA ligase. Optionally, the circular ligase is a thermostable RNA ligase. Optionally, the circular ligase is TS2126 RNA ligase or an adenylated form of TS2126 RNA ligase. Optionally, the circular ligase is CIRCLIGASE™ ssDNA ligase or CIRCLIGASE II™ ssDNA ligase (Epicentre Biotechnologies, Madison, Wis.; Lucks et al., 2011, *Proc. Natl. Acad. Sci. USA* 108:11063-11068; Li et al., 2006, *Anal. Biochem.* 349:242-246; Blondal et al., 2005, *Nucleic Acids Res.* 33:135-142). Optionally, the circular ligase is thermoautotrophicum RNA ligase 1 or "MthRn1 ligase." See, for example, U.S. Pat. Nos. 7,303,901; 9,217,167; and International Publication No. WO2010/094040, each of which are incorporated by reference herein in their entirety. In some embodiments, the ligase used with the hook probes is T4 DNA ligase (e.g., T4 RNA ligase I; Zhang et al., 1996, *Nucleic Acids Res.* 24:990-991; Tessier et al., 1986, *Anal. Biochem.* 158:171-178)). In some embodiments, the ligase used with the hook probes is a thermostable 5' App DNA/RNA ligase.

Formation of Hook Products

Provided herein are methods for producing hook products. Formation of hook products may be used, inter alia, for enriching one or more nucleic acid sequences of interest in a sample comprising a mixture of nucleic acids. Optionally, the formation of hook products can be used to synthesize artificial genes. Hook products comprise a target nucleic acid sequence (e.g., a genomic DNA fragment comprising a sequence of interest) and hook probe sequences at one or both termini of the target nucleic acid sequence. Typically, a hook product contains hook probe sequences at one or both termini of the target nucleic acid fragment.

The methods include providing a ligase (e.g., circular ligase), one or more 5' hook probes comprising a target specific region and a hook region, and/or one or more 3' hook probes comprising a target specific region and a hook region and contacting the sample comprising the nucleic acids with the one or more 5' hook probes, the one or more 3' hook probes, and the circular ligase under conditions to allow the hook probes to selectively bind to the one or more nucleic acid sequences of interest and under conditions to form one or more hook products. In some embodiments, each hook product comprising a 5' hook probe ligated to the 5' terminus of the nucleic acid sequence of interest and a 3' hook probe ligated to the 3' terminus of the nucleic acid sequence of interest. As discussed above, the hook regions of the 5' hook probes can include, for example, a universal primer binding site, a unique molecular identifier, a sample barcode, a cell barcode, or any combination thereof. Similarly, the hook regions of the 3' hook probes can include a universal primer binding site, a unique molecular identifier, a sample barcode, a cell barcode, or any combination thereof.

Formation of hook products comprises contacting the sample comprising the nucleic acids with the one or more 5' hook probes, the one or more 3' hook probes, and the ligase under conditions to allow the hook probes to selectively bind to the one or more nucleic acid sequences of interest and under conditions to form one or more hook products. The sample comprising target polynucleotides and non-target polynucleotides, the ligase, and the hook probes may be combined in any suitable fashion to form a reaction mixture (i.e., the sample comprising the nucleic acids with the one or more 5' hook probes, the one or more 3' hook probes, and the ligase under conditions to allow the hook probes to selectively bind to the one or more nucleic acid sequences of interest and under conditions to form one or more hook products). In some embodiments, the sample is combined with a composition comprising the one or more 5' hook probes and/or one or more 3' hook probes and/or a circular ligase. In some embodiments, the sample is combined with the hook probes followed by addition of the ligase is added a composition comprising the one or more 5' hook probes and/or one or more 3' hook probes and/or a circular ligase. Optionally, the contacting comprises contacting the sample with a reaction mixture comprising the one or more 5' hook probes and the one or more 3' hook probes and further comprises contacting the sample with the circular ligase.

Optionally, the methods further include denaturing the nucleic acids in the sample prior to contacting the reaction mixture with the sample. In some embodiments, the methods further comprise fragmenting the nucleic acids in the sample prior to contacting the reaction mixture with the sample. As noted above, the nucleic acids in the sample can be from any size, for example, the nucleic acids in the sample can have an average length from 100 to 500 nucleotides, or from 100 to 200 nucleotides, or from 400 to 500 nucleotides.

As described herein, the target specific region of the herein provided hook probes (whether 3' or 5') can bind at the terminus or at a location away from the terminus of the nucleic acid sequence of interest. Optionally, the target specific region of the 5' hook probe can bind the nucleic acid sequence of interest at the 5' terminus or at a location from 1 to 200, or more nucleotides from the 5' end of the nucleic acid sequence of interest. For example, the target specific region of the hook probe can bind the nucleic acid sequence of interest at a location from 100 to 200 nucleotides from the 5' end of the nucleic acid sequence of interest. Optionally, the target specific region of the 3' hook probe can bind the nucleic acid sequence of interest at the 5' terminus or at a location from 1 to 200 nucleotides away from the 3' terminus of the nucleic acid sequence of interest. For example, the target specific region of the hook probe can bind the nucleic acid sequence of interest at a location from 100 to 200 nucleotides from the 3' end of the nucleic acid sequence of interest.

FIG. 1 illustrates 5' and 3' hook probes with target sequence regions (also referred to as gene specific regions, or GPS) hybridized to complementary nucleic acid sequences of interest in a target polynucleotide. As illustrated in FIG. 1, in certain embodiments more than one 5' hook probes and/or more than one 3' hook probes can hybridize to the target polynucleotides. At least some of the hook probes hybridize sufficiently close to the terminus of the target polynucleotide that the free end of the hook region is ligated to the target polynucleotide. Thus, the 5' hook probes can include multiple 5' hook probes comprising different target specific regions binding to the same nucleic acid sequence of interest. Optionally, the 5' hook probes comprise a first 5' hook probe comprising a first target specific region binding to a first location in a first nucleic acid sequence of interest and a second 5' hook probe comprising a second target specific region binding to a second location in the first nucleic acid sequence of interest. Similarly, the 3' hook probes can include multiple 3' hook probes comprising different target regions binding to the same nucleic acid sequence of interest. Optionally, the 3' hook probes comprise a first 3' hook probe comprising a first target specific region binding to a first location in a first nucleic acid sequence of interest and a second 3' hook probe comprising a second target specific region binding to a second location in the first nucleic acid sequence of interest. As illustrated in FIG. 1, the hook probes may comprise a sample barcode (SB).

FIG. 2 illustrates an exemplary method using hook probes. DNA (e.g., fragmented genomic DNA or cell-free DNA) can be denatured (e.g., by heat) followed by contacting with one or more hook probes or hook probe sets. The hook probes bind the nucleic acid sequences of interest in the target polynucleotide (identified by the asterisk) and one to three 5' hook probes and one to three 3' hook probes annealed to the target (two pairs of hook probes are shown). The molecular complex is combined with ligase and hook probes are ligated to the termini of the target nucleic acid to form hook products.

Floater ligation products that do not contain target DNA may be formed from unannealed hook probes. Floater ligation products, along with other single stranded nucleic acids, can be degraded using exonucleases. Exemplary suitable exonucleases include 5'→3' exonucleases, 3'→5' exonucleases and exonucleases with both activities. Exemplary suitable exonucleases include Exo VII, ExoI (or ExoT), RecJ, or both ExoI (or ExoT) and RecJ). ExoVII digests single stranded DNA at both 5' and 3' ends, RecJ is a 5'→3' exonuclease, ExoI and ExoT are 3'→5' exonucleases. The exonuclease treatment also degrades hook probes or off target ssDNA (DNA without hook probe sequences). As illustrated in FIG. 2, the hook produce may be amplified using primers (e.g., universal primers that hybridize to, or are complementary to, primer sequences from the hook probe hook regions. In some embodiments the amplicons are sequenced. In FIG. 2, the "X" illustrates the position of a biologically significant variation.

In some embodiments, the method includes using only 5' hook probes or only 3' hook probes. Thus, provided is a method for enriching for one or more nucleic acid sequences of interest in a sample comprising nucleic acids including providing one or more 5' hook probes comprising a target specific region and a hook region and a circular ligase, and contacting the sample comprising the nucleic acids with the one or more 5' hook probes, and the circular ligase under conditions to allow the 5' hook probes to selectively bind to the one or more nucleic acid sequences of interest and under conditions to form one or more hook products. Optionally, each hook product comprising a 5' hook probe ligated to the 5' terminus of the nucleic acid sequence of interest.

Also provided is a method for enriching for one or more nucleic acid sequences of interest in a sample comprising nucleic acids, including providing one or more 3' hook probes comprising a target specific region and a hook region and a circular ligase, and contacting the sample comprising the nucleic acids with the one or more 3' hook probes, and the circular ligase under conditions to allow the 3' hook probes to selectively bind to the one or more nucleic acid sequences of interest and under conditions to form one or more hook products. Optionally, each hook product comprising a 3' hook probe ligated to the 3' terminus of the nucleic acid sequence of interest.

Figure 3:
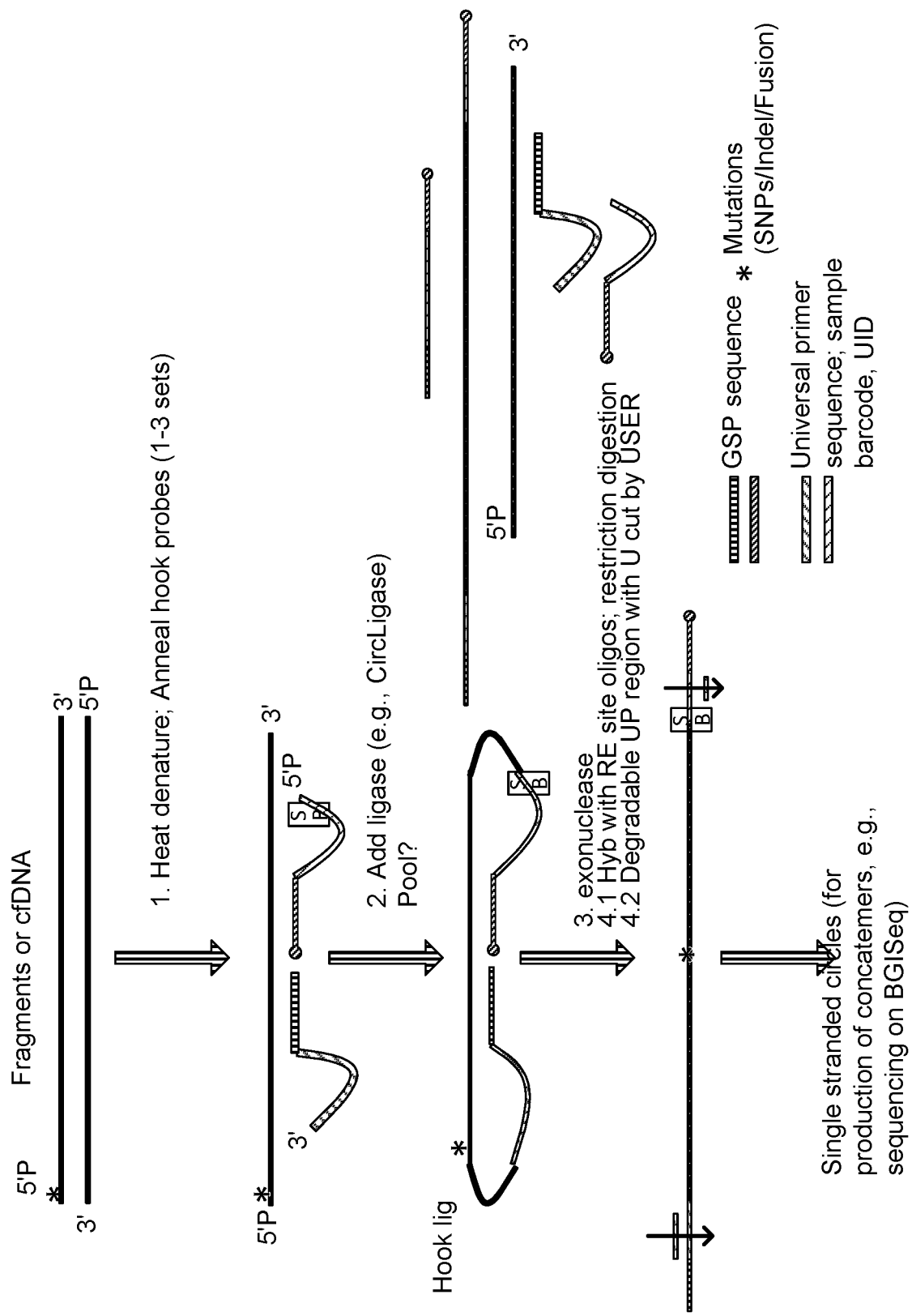
FIG. 3 is a schematic of an exemplary PCR-free method using hook probes that include a restriction enzyme site or a modified nucleotide (e.g., U) that is capable of being cleaved by one or more enzymes (e.g., Uracil Specific Excision Reagent (USER) which facilitates removal of the target specific regions of the hook probes.
Figure 9:
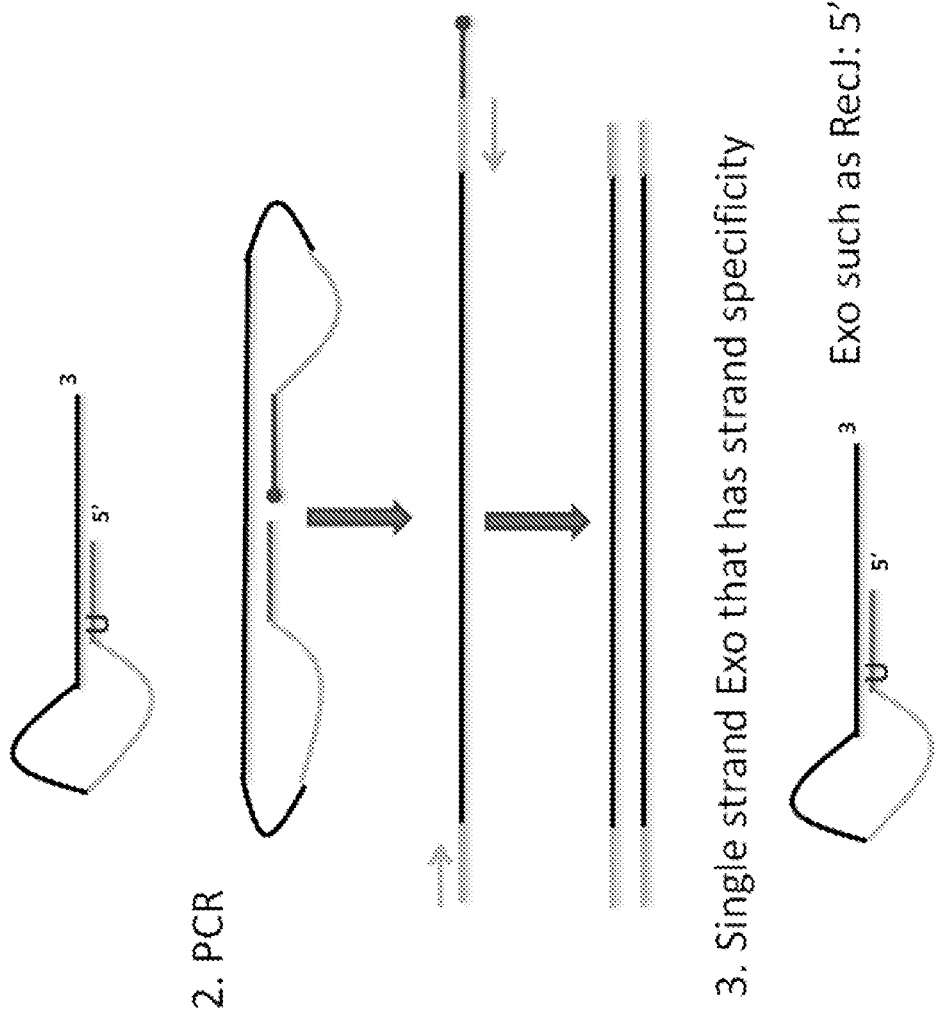
FIG. 9 is a schematic showing an exemplary method using hook probes. In this instance, the hook probes contain a degradable nucleotide or a restriction enzyme or nicking site (the degradable nucleotide U is shown). The hook probes bind the nucleic acid sequence of interest and a hook probe is ligated to the terminus of the target nucleic acid to form hook products. Hook products can be amplified using universal primers. Floater ligation products containing non-target DNA, along with other single stranded nucleic acids, can be degraded using exonucleases.

FIG. 3 is a schematic of an exemplary PCR-free method using hook probes. DNA (e.g., fragmented genomic DNA or cell-free DNA) can be denatured (e.g., by heat or alkaline) followed by contacting with one or more hook probes or hook probe sets. The hook probes bind the nucleic acid sequences of interest (represented by the asterisk) and one 5' hook probe and one 3' hook probe are ligated to the 5' and 3' termini, respectively, of the target nucleic acid to form hook products. Floater ligation products containing non-target DNA, along with other single stranded nucleic acids, can be degraded using single-stranded specific exonucleases. In this figure, hook probes include a restriction enzyme (RE) recognition site capable of being cleaved by a restriction enzyme, or a modified nucleotide (e.g., U) is capable of being cleaved by one or more enzymes (e.g., Uracil Specific Excision Reagent (USER)). This facilitates removal of the target specific regions of the hook probes. If desired, the hook products can be ligated to form circles capable of being amplified by rolling circle amplification. FIG. 9 also shows an exemplary method using hook probes that contain a degradable nucleotide or a restriction enzyme or nicking site (the degradable nucleotide U is shown). The hook probes bind the nucleic acid sequence of interest and a hook probe is ligated to the terminus of the target nucleic acid to form hook products. Hook products can be amplified using universal primers. Floater ligation products containing non-target DNA, along with other single stranded nucleic acids, can be degraded using exonucleases.

Figure 4:
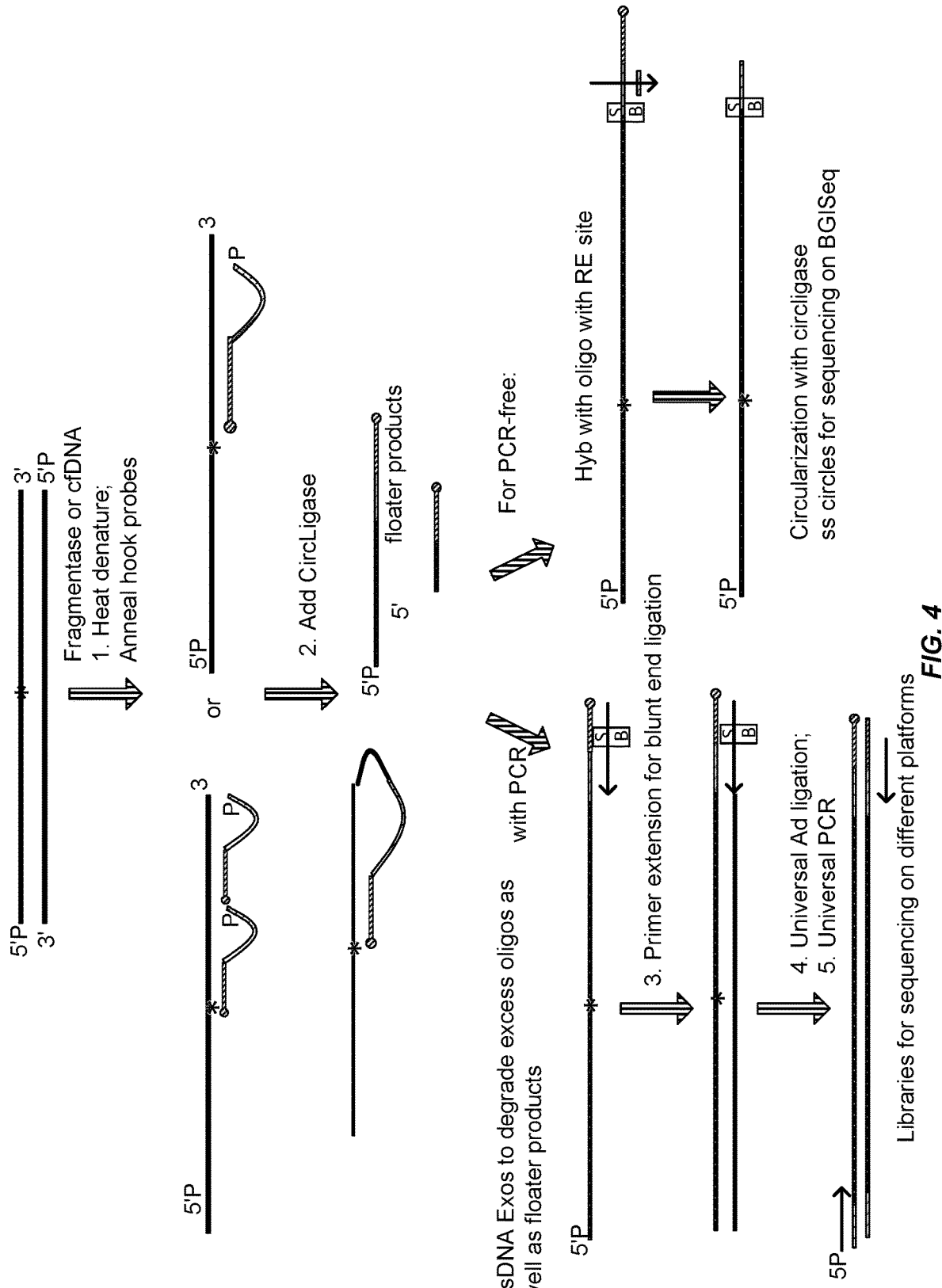
FIG. 4 is a schematic of an exemplary method using hook probes in which hook products are amplified using PCR or, e.g., by rolling circle amplification.

FIG. 4 is a schematic of an exemplary method using hook probes. DNA (e.g., fragmented genomic DNA or cell-free DNA) can be denatured (e.g., by heat) followed by contacting with one or more 5' hook probes or one or more 3' hook probes (3' hook probes are shown). The hook probes bind the nucleic acid sequences of interest (represented by the asterisk) and a hook probe is ligated to the terminus of the target nucleic acid. Floater ligation products containing non-target DNA, along with other single stranded nucleic acids, can be degraded using exonucleases. The hook products can be denatured and extended using a universal primer (optionally containing a sample barcode (SB)). In one approach universal adapter sequences are ligated to the extended products and further amplified using universal primers. Alternatively, the hook products are digested with a restriction enzyme or other enzyme to remove at least a portion of the target specific region of the hook products. The hook products can be circularized to form single-stranded circles ready for amplification, e.g., by rolling circle amplification.

Figure 5:
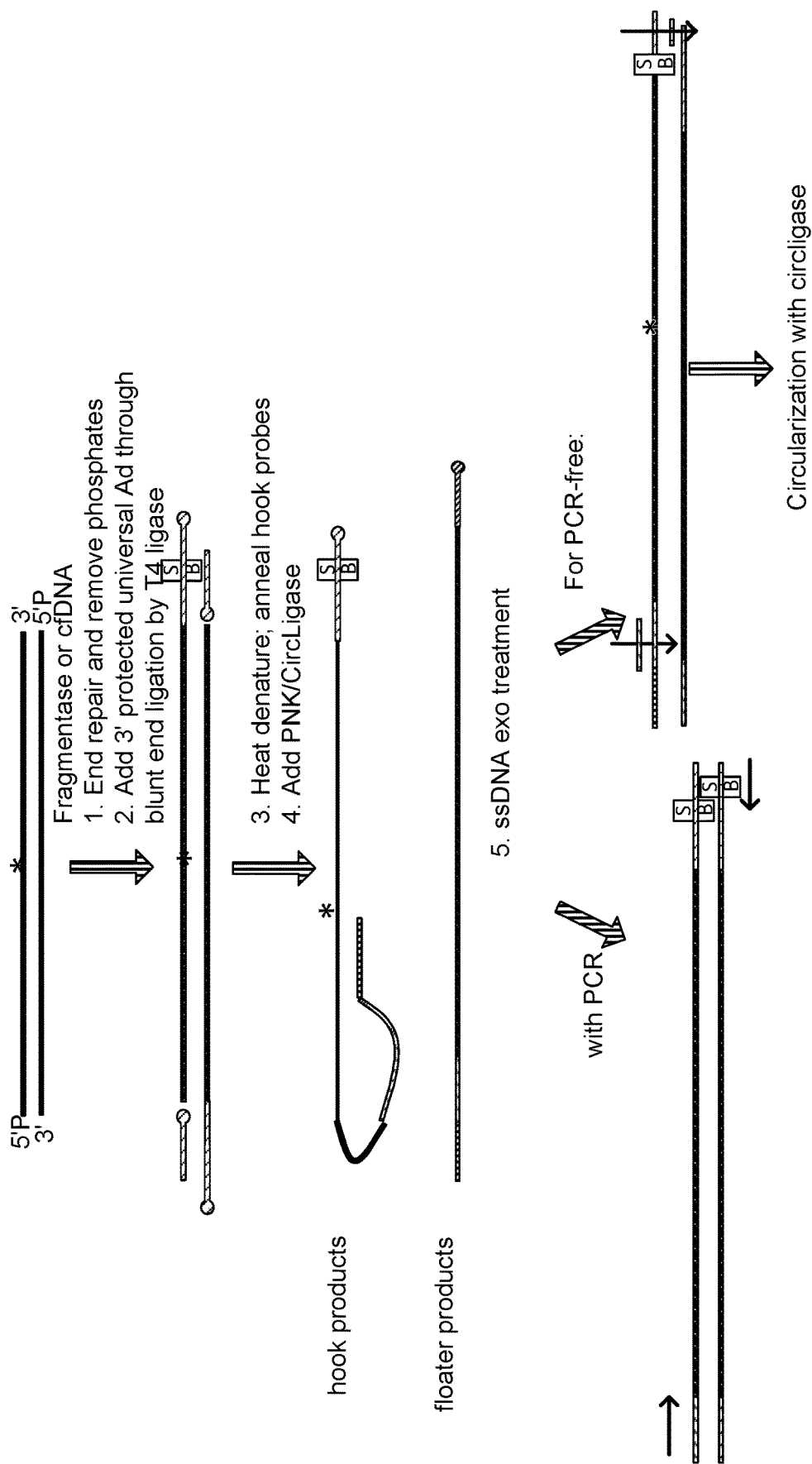
FIG. 5 is a schematic of an exemplary method using hook probes in which DNA (e.g., fragmented genomic DNA or cell-free DNA) is subjected to end repair and phosphate removal to produce blunt end double stranded nucleic acids.

FIG. 5 is a schematic of an exemplary method using hook probes. DNA (e.g., fragmented genomic DNA or cell-free DNA) is subjected to end repair and phosphate removal to produce blunt end double stranded nucleic acids. Universal adapters are ligated to the double stranded fragments. These fragments are denatured and contacted with one or more 5' hook probes or one or more 3' hook probes (5' hook probes are shown) to form hook products. Floater ligation products containing non-target DNA, along with other single stranded nucleic acids, can be degraded using exonucleases. The hook products can be amplified using universal primers or cleaved to remove the target specific region followed by circularization.

Figure 6:
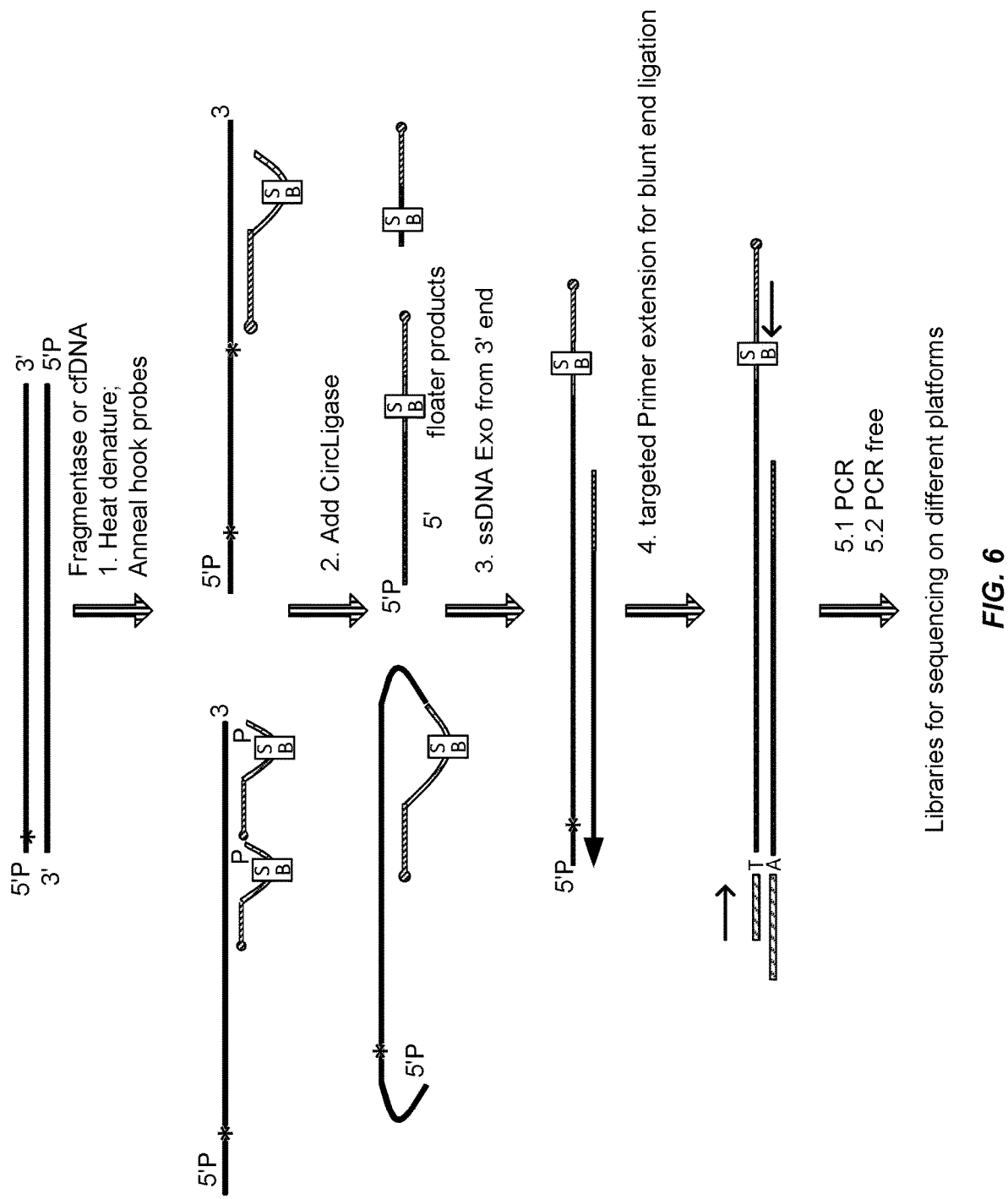
FIG. 6 is a schematic of an exemplary method using hook probes extension products produced from the hook products.

FIG. 6 is a schematic of an exemplary method using hook probes. DNA (e.g., fragmented genomic DNA or cell-free DNA) can be denatured (e.g., by heat) followed by contacting with one or more 5' hook probes or one or more 3' hook probes (3' hook probes are shown). The hook probes bind the nucleic acid sequences of interest (represented by the asterisk) and a hook probe is ligated to the terminus of the target nucleic acid to form hook products. Floater ligation products containing non-target DNA, along with other single stranded nucleic acids, can be degraded using exonucleases. In this example, extension products are produced using a target specific primer to prepare the products for adapter ligation. The products are optionally amplified.

Contacting

The sample comprising the nucleic acid sequences of interest can be contacted with the circular ligase and the 5' and/or 3' hook probes in any order or combination. In one approach the ligase and hook probes may be combined and the combination added to the sample. In some embodiments, the sample is contacted simultaneously with the circular ligase and the 5' and/or 3' hook probes. In some embodiments, contacting comprises contacting the sample with a reaction mixture comprising the one or more 5' hook probes. Optionally, the reaction mixture further comprises the one or more 3' hook probes. Optionally, the reaction mixture further comprises the circular ligase. For example, the contacting can include contacting the sample with a reaction mixture comprising the one or more 5' hook probes and/or the one or more 3' hook probes and further includes contacting the sample with a reaction mixture comprising the circular ligase. The circular ligase can be contacted with the sample before, at the same time or after addition of the 5' and/or 3' hook probes. In some embodiments, the contacting comprises contacting the sample with the one or more 5' hook probes and the circular ligase under conditions to allow the 5' hook probes to bind to a first nucleic acid sequence of interest and to ligate a 5' hook probe to the 5' terminus of the first nucleic acid sequence of interest and contacting the sample with the one or more 3' hook probes under conditions to allow the 3' hook probes to bind to the first nucleic acid sequence of interest and to ligate a 3' hook probe to the 3' terminus of the first nucleic acid sequence of interest. Optionally, the 3' hook probes are added to the sample and ligated to a nucleic acid sequence of interest prior to addition of the 5' hook probes. The circular ligase can be added before, at the same time, or after the hook probes and addition of the circular ligase to the sample can be repeated as desired. Similarly, contacting the sample with the 5' and/or 3' hook probes can be performed repeatedly as desired.

Multiplexing and Massively Parallel Enrichment

Although for clarity FIG. 2 illustrates a single target nucleic acid it will be appreciated that most often a plurality of different target nucleic acid fragments, comprising different sequences of interest, are converted to hook products. In various embodiments, from 2 to 50,000 or more different sequences of interest can be incorporated into hook products in a single reaction mixture.

Random Sequence Embodiments

In several embodiments described herein, the target specific region is designed to bind to a predetermined sequence (e.g., a specific genomic or synthetic sequence) or sequences (a small number of related genomic sequences). In other embodiments, a hook probe or library of hook probes may comprise degenerate or random sequence target non-specific regions. Such a library can be used, for example, to produce a population of hook products that characterize a whole genome without knowledge of the specific correspondence of the population of hook products. Similarly, a library of random sequence hook probes could be used to detect different alleles or copy number variations based on a pattern of hook products produced.

Circular Nucleic Acid Molecules

Figure 7:
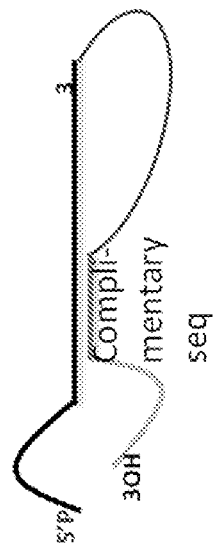
FIG. 7 is a schematic showing formation of a circular DNA molecule by ligation of the ends of a target nucleic acid containing a nucleic acid sequence of interest and complimentary sequences.

FIG. 7 is a schematic showing formation of a circular DNA molecule by ligation of the ends of a target nucleic acid containing a nucleic acid sequence of interest. A portion of the target nucleic acid contains complementary sequences forming a double stranded segment and a loop at one end. At the other end, the 5' and 3' ends of the target nucleic acid are in proximity and capable of being ligated together.

Thus, provided is a method for circularizing a single stranded target nucleic acid comprising a nucleic acid sequence of interest. In some embodiments, the target nucleic acid is greater than 500 nucleotides in length. In some embodiments, the method includes providing a target nucleic acid comprising a first region and a second region separated by 1 to 500 nucleotides or more than 500 nucleotides, the first and second regions are complementary to each other and capable of forming a double stranded structure. The method also includes providing a ligase, and contacting the target nucleic acid with the ligase under conditions to form a ligation product. The ligation product formed by the method is a circular target nucleic acid containing the nucleic acid sequence of interest. The ciruclar target nucleic acid has a dumbbell structure with two single stranded regions flanking a double stranded region formed by the complimentary sequences of the target nucleic acid.

Methods of Using Hook Probes

In some embodiments, the method for enriching for at least one nucleic acid sequences of interest in a sample comprising nucleic acids includes providing a ligase, providing at least one 5' hook probe and at least one 3' hook probe, each hook probe comprising a target specific region and a hook region. In some embodiments, the hook probe is suitable for ligating the hook region to the nucleic acid sequence of interest when the target specific region of the hook probe is hybridized to the nucleic acid sequence of interest. In some embodiments, the target specific region is a known, specific sequence, or when multiple probes are used a panel of known specific sequences. Optionally, the target specific region can be random sequences. The hook probes are contacted with the sample and the ligase under conditions to allow the hook probes to selectively bind to the one or more nucleic acid sequences of interest and under conditions to form one or more hook products, each hook product comprising a 5' hook probe ligated to the 5' terminus of the nucleic acid sequence of interest and a 3' hook probe ligated to the 3' terminus of the nucleic acid sequence of interest.

The provided methods can include digesting single stranded nucleic acids that do not include nucleic acid sequences of interest, for example, non- or off-target DNA. The provided methods can also include digesting any non-ligated hook probes and random ligation products. See, for example, FIG. 2. Thus, the provided methods can include contacting the hook products with one or more exonucleases. Suitable exonucleases are known and commercially available. Exonucleases include, but are not limited to, Exo VII, RecJ, ExoI of ExoT. The provided methods, composition, reaction mixtures and kits can include one or more exonucleases. Thus, the hook products can be contacted with Exo VII, RecJ, ExoI, ExoT, or any combination thereof. The exonucleases digest single stranded nucleic acids. Optionally, the exonucleases do not digest the one or more hook products. Optionally, the method further comprises purifying the hook products. Optionally, the hook products are purified using magnetic beads. For example, the hook products are purified using magnetic beads comprising an oligonucleotide complementary to a portion of a hook product. The hook products bind the appropriate oligonucleotide located on the magnetic bead. The magnetic beads with the hook products are then isolated and the hook products are obtained from the magnetic beads thereby purifying the hook products.

As described throughout, the reaction mixtures can include any number of 5' and/or 3' hook probes. Optionally, the reaction mixture comprises 1, 2, 3, 4, or 5 5' hook probes. Optionally, the reaction mixture comprises 1, 2, 3, 4, or 5 3' hook probes. Optionally, the reaction mixture comprises 6, 7, 8, 9, 10, 15, 20, 25, 30, 35, 40, 45, or 50 5' hook probes. Optionally, the reaction mixture comprises 6, 7, 8, 9, 10, 15, 20, 25, 30, 35, 40, 45, or 50 3' hook probes. Optionally, the reaction mixture comprises 2 5' hook probes and 2 3' hook probes. Optionally, the reaction mixture comprises 3 5' hook probes and 3 3' hook probes. Optionally, the reaction mixture comprises 1 5' hook probe and 1 3' hook probe.

As used in the provided methods, the 5' hook probes can include a 3'OH group, a 5' blocking group or any combination thereof. Optionally, the 3' hook probe comprises a 5' phosphate, a 3' blocking group or any combination thereof.

In some embodiments, the universal priming site is from 5 to 30 nucleotides in length. Optionally, the unique molecular identifier is from 1, 2, 3, 4, 5, 6, 7, 8, 9, 10, 11, 12, 13, 14, or 15 nucleotides in length.

Modification and Use of Hook Products

As described throughout, once hook products are formed the hook products containing the nucleic acid sequences of interest may be processed in any number of ways including amplification, adapter ligation or any combination thereof. Optionally, the hook products are used to generate a library of nucleic acid sequences of interest for sequencing analysis. Optionally, the hook products are used for synthesis of artificial genes. Optionally, the hook products are amplified (e.g., using universal primers binding to the universal primer binding site on the hook probes). Optionally, the universal primers and/or the hook probes can include a sample barcode. Thus, the provided methods can include annealing universal primers to the enriched nucleic acid sequences of interest and amplifying the nucleic acid sequences of interest. Optionally, the hook products are processed to remove the target specific regions of the hook probes and are circularized to produce single stranded circular nucleic acid sequences of interest. Optionally, the circularized nucleic acid sequences of interest are amplified by rolling circle amplification.

The hook products containing the nucleic acid sequences of interested can be modified by ligating adapters to the 5' and/or 3' ends of the nucleic acid sequences of interest. Optionally, the amplified hook products can be ligated with adapters. Thus, the provided methods can include ligating adapters to the enriched nucleic acid sequences of interest. Optionally, the adapters are ligated to the 5' and/or 3' ends of the nucleic acid sequences of interest. Optionally, the adapters are ligated to the enriched nucleic acid sequences of interest after amplification, i.e., to the amplified enriched nucleic acid sequences of interest.

Methods for amplification and adapter ligation to nucleic acid sequences of interest are known. For example, in many massively parallel sequencing (MPS) technologies, a library of sequencing templates is generated and individual species in the library are sequenced in parallel. For example, in the DNA nanoball approach, genomic DNA is fragmented, and individual fragments are used to produce circular DNAs in which platform-specific oligonucleotide adapters separate genomic DNA sequences (which separated genomic DNA sequences may be contiguous in the genome). The circular DNAs are amplified to generate single-stranded concatemers ("DNA nanoballs") which may be immobilized on a substrate. In another sequencing approach, genomic DNA is fragmented and the DNA fragments are then ligated to platform-specific oligonucleotide adapters. The adaptors are used to immobilize individual fragments on a substrate where they are amplified in situ to produce clonally clustered amplicons for sequencing. Many other MPS sequencing approaches are known.

Thus, it will be recognized that, although, the present invention is sometimes described in terms of a target DNA (e.g., a single DNB template DNA), MPS sequencing is carried out using a large libraries of sequences, typically on arrays (e.g., arrays comprising DNA concatemers or clonal copies of the template DNA polynucleotides) of constructs comprising numerous different target sequences (e.g., different genomic DNA fragments) but sharing common adaptor sequences.

Method for making MPS sequencing libraries, and methods of sequencing using such libraries, are well known in the art, and familiarity by the reader with such methods is assumed. See, for illustration and not limitation, Shendure, J. and H. Ji. "Next-generation DNA sequencing," Nature biotechnology 26.10 (2008): 1135-1145; Shendure, J., et al. "Advanced sequencing technologies: methods and goals" Nat. Rev. Genet. 5, 335-344 (2004); Metzker, Michael L. "Sequencing technologies—the next generation," Nature Reviews Genetics 11.1 (2010): 31-46; Drmanac, R. et al. "Accurate Whole Genome Sequencing as the Ultimate Genetic Test," Clinical Chemistry 61.1 (2015): 305-306; Drmanac, R. et al. "Human genome sequencing using unchained base reads on self-assembling DNA nanoarrays," Science 327.5961 (2010): 78-81; Drmanac, S. et al. "Accurate sequencing by hybridization for DNA diagnostics and individual genomics," Nat. Biotechnol. 16, 54-58 (1998); Margulies, M. et al. "Genome sequencing in microfabricated high-density picolitre reactors," Nature 437.7057 (2005): 376-380; Ng, S. et al. "Targeted capture and massively parallel sequencing of 12 human exomes," Nature 461.7261 (2009): 272-276; Meng, H-M et al. "DNA dendrimer: an efficient nanocarrier of functional nucleic acids for intracellular molecular sensing," ACS Nano 8.6 (2014): 6171-6181; Shendure, J. et al. "Accurate multiplex polony sequencing of an evolved bacterial genome," Science 309, 1728-1732 (2005); Brenner, S. et al. "Gene expression analysis by massively parallel signature sequencing (MPSS) on microbead arrays" Nat. Biotechnol. 18, 630-634 (2000); Ronaghi et al. "Real-time DNA sequencing using detection of pyrophosphate release" Anal. Biochem. 242, 84-89 (1996); McKernan, K. et al. "Reagents, methods, and libraries for bead-based sequencing," U.S. Patent Application Publication No. 2008/0003571 (2006); Adessi, C. et al. "Solid phase DNA amplification: characterisation of primer attachment and amplification mechanisms" Nucleic Acids Res. 28, e87 (2000), each of which is incorporated in its entirely for all purposes, including for teaching preparation of DNA sequencing libraries and MPS sequencing platforms and techniques.

In some embodiments, the method comprises purifying and capturing the hook products. Optionally, the hook products are purified using magnetic beads or biotinylated beads.

Compositions and Kits

For example, composition, reaction mixture, or kit, can be provided that contains from 1 to 50,000 or more hook probes. In some cases, the composition, reaction mixture, or kit contains from 2 to 40,000, from 2 to 30,000; from 2 to 25,000; from 2 to 20,000; from 2 to 15,000; from 2 to 10,000; from 2 to 7,500; from 2 to 5,000; from 2 to 2,500; from 2 to 1,000; from 2 to 500; from 2 to 250; from 2 to 200; from 2 to 150; from 2 to 125; from 2 to 100; from 2 to 75; from 2 to 50; from 2 to 25, or from 2 to 10 different hook probes. In some cases, the composition, reaction mixture, or kit contains from 10 to 40,000, from 10 to 30,000; from 10 to 25,000; from 10 to 20,000; from 10 to 15,000; from 10 to 10,000; from 10 to 7,500; from 10 to 5,000; from 10 to 2,500; from 10 to 1,000; from 10 to 500; from 10 to 250; from 10 to 200; from 10 to 150; from 10 to 125; from 10 to 100; from 10 to 75; from 10 to 50; from 10 to 25, or from 10 to 20 different hook probes. In some cases, the composition, reaction mixture, or kit contains, contains about, contains at least, or contains at least about 10; 20; 30; 40; 50; 75; 100; 200; 250; 300; 400; 500; 750; 1,000; 2,000; 3,000; 4,000; 5,000; 7,500; 10,000; 15,000; or more than 15,000 different hook probes.

In some cases, the plurality of different hook probes is a panel of hook probes directed to a specific subset of target nucleic acids. For example, the hook probes can be a cancer panel directed to, e.g., genomic, regions of DNA known to affect cancer risk of an organism. As another example, the hook probes can be an exome or transcriptome panel directed to a substantial portion, or all, of the exome sequences or transcriptome sequences of an organism of interest. As yet another example, the hook probes can be a panel of hook probes for enrichment of nucleic acids that indicate the presence of a pathogen, or a group of pathogens, and/or virulence markers associated with such a pathogen or group of pathogens.

Thus, hook probes can be used to enrich for a large number of nucleic acids of interest. For example, hook probes can be used to enrich from 1 to 10; 1 to 10,000; 10 to 15,000; 10 to 50,000; 10 to 100,000; 1,000 to 10,000; 1,000 to 15,000; 1,000 to 50,000; 1,000 to 100,000; or more nucleic acid sequences of interest. The enrichment of a large number of nucleic acid sequences of interest from a sample can be useful for, e.g., genome-wide, exome-wide, or transcriptome-wide nucleic acid sequence analysis, analysis of target organism populations, or analysis of environmental samples. Thus, hook probes can be used to enrich for nucleic acid sequences of interest to generate a library of nucleic acids for sequence analysis. Library generation can include amplification of the enriched nucleic acid sequences of interest; however, such amplification is not necessary for library generation. The provided methods increase the specificity of the library preparation (e.g., as indicated by the percent of on-target reads produced in a subsequent sequencing step). The libraries generated using the provided hook probes are compatible with high-throughput sequencing platforms including, but not limited to, sequencing by ligation (e.g., combinatorial probe anchor ligation (cPAL)) or sequencing by synthesis, methods known in the art. It will be recognized that sequencing libraries having essentially any desired adaptor sequences may be prepared.

The herein provided reaction mixtures include one or more 5' hook probes and/or one or more 3' hook probes and a circular ligase.

Also provided are kits comprising one or more 5' hook probe, one or more 3' hook probe or any combination thereof and instructions for use. The kits can include 5' and 3' hook probes in the same or separate containers. Optionally, the kits comprise 1, 2, 3, 4, 5, 6, 7, 8, 9, 10, 15, 20, 25, 30, 35, 40, 45, 50, 75, 100, 125, 150, 175, 200, 225, 250, 275, 300, 325, 350, 375, 400, 425, 450, 475, or 500 5' hook probes. Optionally, the kits comprise 1, 2, 3, 4, 5, 6, 7, 8, 9, 10, 15, 20, 25, 30, 35, 40, 45, 50, 75, 100, 125, 150, 175, 200, 225, 250, 275, 300, 325, 350, 375, 400, 425, 450, 475, or 500 3' hook probes. Optionally, the kits comprise 2 5' hook probes and 2 3' hook probes. Optionally, the kits comprise 3 5' hook probes and 3 3' hook probes. Optionally, the kits comprise 1 5' hook probe and 1 3' hook probe. In some embodiments, depending on the application, the kit contains 500, 1000, 2000, 3000, 4000, 5000, 6000, 7000, 8000, 9000, 10,000, 15,000, 20,000 or more probes. The kits may further include in the same or separate containers enzymes for performing the provided methods including, for example, the circular ligase, restriction enzymes, exonucleases or any combination thereof. The kits can include primers, adapters or other nucleic acids and/or enzymes or other reagents necessary for amplification of the nucleic acid sequences of interest. Thus, the kits can include adapters, universal primers or any combination thereof. The kits can also include enzymes such as polymerases and reagents for amplification of the nucleic acid sequences of interest.

Splint Oligonucleotides

Figure 8:
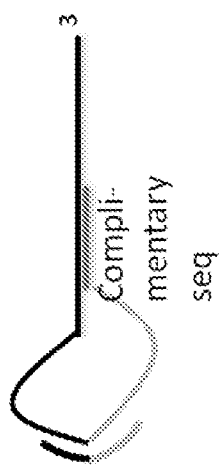
FIG. 8 is a schematic showing the use of a splint oligonucleotide to bring the end of a hook probe and the end of a nucleic acid sequence of interest into proximity for ligation.

In some embodiments, the herein provided reaction mixtures include one or more 5' hook probes and/or one or more 3' hook probes and a splint oligonucleotide. See, e.g., FIG. 8. The splint oligonucleotide hybridizes to the target nucleic acid sequence of interest and to the hook region of the hook probe to bring the terminus of the target nucleic acid sequence of interest and the terminus of the hook probe into proximity to facilitate ligation.

EXAMPLES

Example 1. Target Enrichment Using Hook Probe Ligation

To isolate target nucleic acids using hook probes, a genomic DNA sample is processed by physical or enzymatic fragmentation into 100 bp to 500 bp fragments. Hook probes are contacted with the DNA sample, and hook products are formed using a circular ligase. The hook products can be amplified by PCR or purified using beads and then amplified by PCR. ssDNA can be removed using exonucleases. For example, 10 ng template DNA is heat denatured along with hook probes (no less than 0.1 nM/each probe) in hook ligation buffer at 95° C. for 5-10 minutes. The temperature is reduced to 50° C. (could be any temperature between 25° C. to 60° C.) for 1 hour (could incubate longer than 4 hours). A circular ligase is added at 50° C. (could be any temperature between 25° C. to 60° C.) for 1 hour (could incubate longer than 4 hours). The hook products formed after ligation are purified with magnetic beads and the DNA is eluted into a certain volume, for example, 40 µl. Enriched nucleic acid sequences of interest are amplified using universal primers by PCR.

Example 2. Hook Probe Ligation Efficiency

To determine the ligation efficiency of hook probes, 10% denaturing polyacrylamide gel (TBU gel) was used to show the hook ligation efficiency mediated by circLigase I (Epicenter, Madison, Wis.) on a 90 base pair synthetic DNA (YJ-439).

Figure 10:
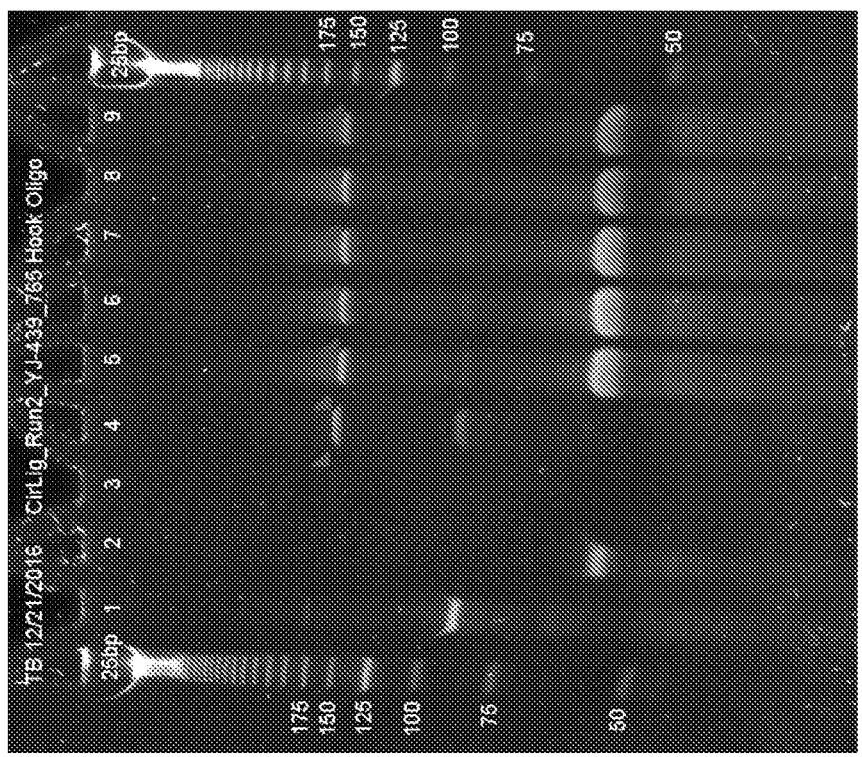
FIG. 10 is an image of a gel showing ligation products between a nucleic acid sequence of interest and a 5' hook probe.

FIG. 10 is an image of the gel showing YJ-439 in lane 1 (synthesized by IDT) and a target specific 5' hook probe, YJ-765 in lane 2 (synthesized by IDT). YJ-439 formed single stranded circles (labeled by arrowheads in lanes 3 and 4) by itself at its optimal temperature of 55° C., in lane 3 (with Exonuclease I and III treatment) and lane 4 (without Exonuclease I and III treatment). When incubated with hook probes (YJ-765) at different temperatures as shown in lanes 5-9 (25° C., 37° C., 45° C., 55° C. and 60° C., respectively), the majority of YJ-439 formed hook ligation products (labeled by arrowheads in lanes 5-9) instead of single stranded circles. The hook ligation products were degraded by Exonuclease I and III (data not shown), suggesting that the ligation products were linear products.

YJ-439

(SEQ ID NO: 1)
5'-CTCATGCCCTTCGGCTGCCTCCTGGACTATGTCCGGGAACACAAAGA

Caatattggctcccagtacctgctcaactggtgtgtgcagatc

YJ-765 5'_hook probe (SEQ ID NO: 2)
CAGGAGGCAGCCGAAGGGCAGAACGACATGGCTACGATCCGACTTNNNNN

NCATTTCAT

Figure 11:
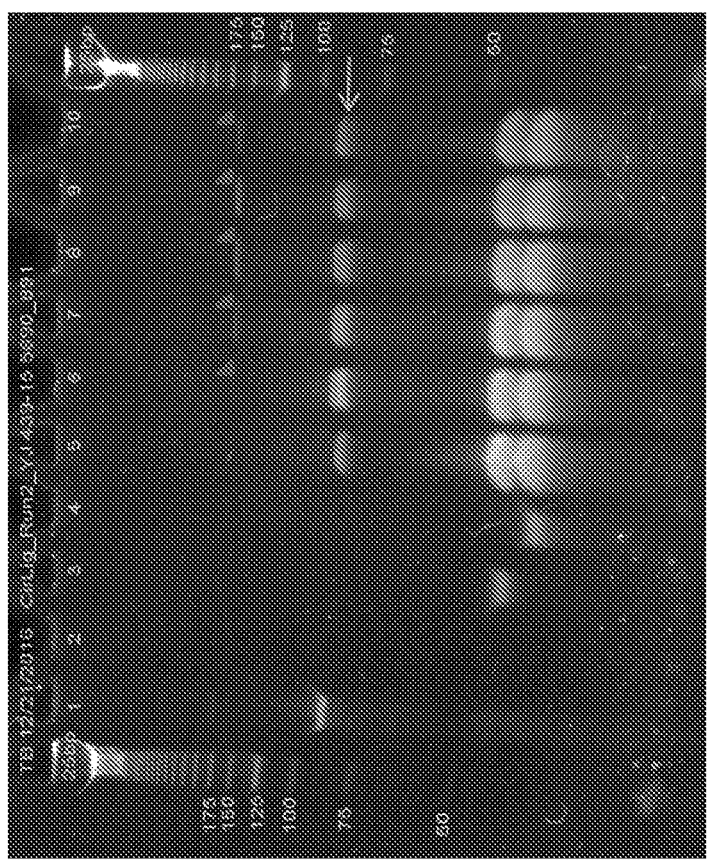
FIG. 11 is an image of a gel showing ligation products between a nucleic acid sequence of interest and 5' and 3' hook probes.

FIG. 11 is an image of a 10% denaturing polyacrylamide gel (TBU gel) showing no or low random hook ligation efficiency mediated by circLigase I (Epicenter, Madison, Wis.) on the 90 base pair synthetic DNA, YJ-439. The 5' and 3' hook probes were YJ-890 (5' hook probe) and YJ-891 (3' hook probe), containing random sequences as the target specific regions (lane 3 and 4 respectively, synthesized by IDT). Lane 5 depicted ligase reactions between hook probes, YJ-890 and YJ-891. YJ-439 formed single stranded circles (labeled by arrowheads) by itself at its optimal temperature, 55° C., in lane 2 (with Exonuclease I and III treatment). When incubated with random hook probes (YJ-890 and 891) at different temperatures as shown in lane 5-9 (25° C., 37° C., 45° C., 55° C. and 60° C., respectively), the majority ligation products were single stranded circles (labeled by arrowheads) that were not susceptible to Exonuclease treatment (data not shown). The random ligation products were not visible on the gel. The 5' and 3' hook probes can form intermolecular ligation products (labeled by the long arrow in lanes 5-10), which were degraded by Exonuclease I and III (data not shown).

YJ-890 (5' hook probe)

(SEQ ID NO: 3)
NNNNNNNNNNNNNNNNNGAACGACATGGCTACGATCCGACTTNNNNNN

YJ-891 (3' hook probe), (SEQ ID NO: 4)
ATGCTGACGGTCAAGTGGTCTTAGGNNNNNNNNNNNNNNNN Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

What is claimed is:

1. A method for producing a hook probe product comprising a nucleic acid sequence of interest, the method comprising
providing one or more 5' hook probes each comprising (1) a hook region not complementary to the nucleic acid sequence of interest and (2) a single-stranded target-specific region complementary to the nucleic acid sequence of interest,
and one or more 3' hook probes, each comprising (1) a hook region not complementary to the nucleic acid sequence of interest and (2) a single-stranded target-specific region complementary to the nucleic acid sequence of interest,
combining: a heterogeneous mixture of nucleic acid fragments comprising different nucleic acid sequences with the one or more 5' hook probes and one or more 3' hook probes, under conditions in which said the at least one or more 5' hook probes and the at least one or more 3' hook probes hybridize specifically to at least a first fragment in the heterogeneous mixture,
wherein the first fragment comprises the nucleic acid sequence of interest, and
ligating one of the 5' hook probes to the 5' terminus of the first fragment and ligating one of the 3' hook probes to the 3' terminus of the first fragment, thereby producing a hook probe product, wherein the hook probe product comprises the nucleic acid sequence of interest.

2. The method of claim 1 wherein the hook region of each of the hook probes comprises a universal primer binding site, a unique molecular identifier, a sample barcode, a cell barcode, or any combination thereof.

3. The method of claim 1 wherein the nucleic acid fragments have an average length from 100 to 500 nucleotides.

4. The method of claim 1 comprising combining said heterogeneous mixture, said one or more hook probes, and a ligase under conditions in which said at least one hook probe specifically hybridizes to the first fragment and said terminus of the hook probe and the terminus of the first fragment ligate together, thereby producing the hook probe product.

5. The method of claim 1 wherein said one or more hook probes comprise multiple hook probes comprising different target specific regions of the same nucleic acid sequence of interest.

6. The method of claim 1 wherein said one or more hook probes comprise a first hook probe comprising a first target-specific region that specifically hybridizes to a first location in the nucleic acid sequence of interest and a second hook probe comprising a second target-specific region that specifically hybridizes to a second location in the nucleic acid sequence of interest.

7. The method of claim 1 wherein said one or more hook probes comprise one or more 5' hook probes and the target-specific region specifically hybridizes to the nucleic acid sequence of interest at the 5' terminus, or at a location from 1 to 200 nucleotides away from the 5' terminus, of the nucleic acid sequence of interest.

8. The method of claim 1 wherein said one or more hook probes comprise one or more 3' hook probes and the target-specific region specifically hybridizes to the nucleic acid sequence of interest at the 3' terminus, or at a location from 1 to 200 nucleotides away from the 3' terminus, of the nucleic acid sequence of interest.

9. The method of claim 1 further comprising contacting the hook probe product with one or more exonucleases.

10. The method of claim 9 wherein said one or more exonucleases digest single stranded nucleic acids.

11. The method of claim 1 wherein said one or more hook probes comprise a 5' hook probe that comprises a 3'—OH group, a 5' blocking group, or both.

12. The method of claim 1 wherein said one or more hook probes comprise a 3' hook probe that comprises a 5'-phosphate group, a 3' blocking group, or both.

13. The method of claim 1 wherein each of said one or more hook probes comprise a restriction enzyme binding site.

14. The method of claim 1 further comprising amplifying the nucleic acid sequence of interest.

15. The method of claim 1 comprising ligating together a terminus of the hook probe and a terminus of the first fragment using a circular ligase selected from the group consisting of TS2126 RNA ligase, an adenylated form of TS2126 RNA ligase, and MthRn1 ligase.

16. The method of claim 1,
wherein ligating is performed using a circular ligase.

17. The method of claim 16 wherein the target specific region is selected from the group consisting of a specific sequence, a panel of specific sequences, and a random sequence.

18. A method of enrichment of a target DNA fragment comprising:
(a) producing a mixture of hook probe products by combining a mixture of genomic nucleic acid fragments with one or more hook 5' probes and one or more 3' probes of the method of claim 1; and then
(b) removing single-stranded genomic fragments from the mixture of hook probe products that are not ligated to any one of the 5' and 3' hook probes.

19. The method of claim 18, wherein the single stranded fragments are removed in step (b) by adding to the mixture of hook probe products one or more exonucleases that digest single stranded nucleic acids.

* * * * *

SEQUENCE LISTING

<160> NUMBER OF SEQ ID NOS: 4

<210> SEQ ID NO 1
<211> LENGTH: 90
<212> TYPE: DNA
<213> ORGANISM: Artificial Sequence
<220> FEATURE:
<223> OTHER INFORMATION: Synthetic construct

<400> SEQUENCE: 1
ctcatgccct tcggctgcct cctggactat gtccgggaac acaaagacaa tattggctcc     60
cagtacctgc tcaactggtg tgtgcagatc                                      90

<210> SEQ ID NO 2
<211> LENGTH: 59
<212> TYPE: DNA

```
<213> ORGANISM: Artificial Sequence
<220> FEATURE:
<223> OTHER INFORMATION: Synthetic construct
<220> FEATURE:
<221> NAME/KEY: misc_feature
<222> LOCATION: (46)..(51)
<223> OTHER INFORMATION: n is a, c, g, or t

<400> SEQUENCE: 2
caggaggcag ccgaagggca gaacgacatg gctacgatcc gacttnnnnn ncatttcat        59

<210> SEQ ID NO 3
<211> LENGTH: 46
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (41)..(46)
<223> OTHER INFORMATION: n is a, c, g, or t

<400> SEQUENCE: 3
nnnnnnnnnn nnnnngaacg acatggctac gatccgactt nnnnnn        46

<210> SEQ ID NO 4
<211> LENGTH: 40
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (26)..(40)
<223> OTHER INFORMATION: n is a, c, g, or t

<400> SEQUENCE: 4
atgctgacgg tcaagtggtc ttaggnnnnn nnnnnnnnnn        40
```